(12) United States Patent
Cole

(10) Patent No.: US 8,753,354 B2
(45) Date of Patent: *Jun. 17, 2014

(54) ENHANCED FOLLICULAR EXTRACTION PUNCH AND METHOD

(76) Inventor: John P. Cole, Atlanta, GA (US)

(*) Notice: Subject to any disclaimer, the term of this patent is extended or adjusted under 35 U.S.C. 154(b) by 1340 days.

This patent is subject to a terminal disclaimer.

(21) Appl. No.: 11/325,388

(22) Filed: Jan. 3, 2006

(65) Prior Publication Data

US 2006/0178678 A1    Aug. 10, 2006

Related U.S. Application Data

(63) Continuation-in-part of application No. 10/795,835, filed on Mar. 9, 2004, now Pat. No. 7,172,604.

(30) Foreign Application Priority Data

Jul. 21, 2004    (WO) ................ PCT/US2004/023533

(51) Int. Cl.
*A61B 17/50*    (2006.01)

(52) U.S. Cl.
USPC ........................................ 606/131

(58) Field of Classification Search
USPC ......... 606/133, 131, 187, 184, 185, 167, 132, 606/170, 172, 176–181
See application file for complete search history.

(56) References Cited

U.S. PATENT DOCUMENTS

| | | | |
|---|---|---|---|
| 2,360,051 A * | 10/1944 | Eweson | 606/131 |
| 3,035,580 A * | 5/1962 | Guiorguiev | 606/44 |
| 3,913,566 A | 10/1975 | Lacey | |
| 3,990,453 A | 11/1976 | Douvas et al. | |
| 3,998,230 A | 12/1976 | Miller | |
| 4,263,913 A | 4/1981 | Malmin | |
| 4,476,864 A | 10/1984 | Tezel | |
| 4,479,445 A | 10/1984 | Walker | |
| 4,798,213 A | 1/1989 | Doppelt | |
| 4,873,991 A | 10/1989 | Skinner | |
| 4,994,028 A | 2/1991 | Leonard et al. | |
| 5,269,316 A | 12/1993 | Spitainy | |
| 5,417,683 A | 5/1995 | Shiao | |
| 5,423,330 A | 6/1995 | Lee | |
| 5,439,475 A | 8/1995 | Bennett | |
| 5,507,765 A | 4/1996 | Mott | |

(Continued)

FOREIGN PATENT DOCUMENTS

| | | |
|---|---|---|
| FR | 2744624 | 8/1997 |
| FR | 2744624 A | 8/1997 |

(Continued)

OTHER PUBLICATIONS

Unger et al., "Hair Transplantation", Fourth Edition, Revised and Expanded, pp. 353-354, Jan. 1, 2004.

(Continued)

*Primary Examiner* — Tuan V Nguyen
*Assistant Examiner* — Tin Nguyen
(74) *Attorney, Agent, or Firm* — Berkeley Law & Technology Group, LLP

(57) ABSTRACT

Provided herein is an apparatus and method useful for surgical removal of mammalian tissue at specific depths and specific angles. In one or more implementations, an extraction instrument having a main body, a nipple portion, a punch, and an actuator may be utilized to extract one or more hair follicles.

20 Claims, 18 Drawing Sheets

(56) References Cited

U.S. PATENT DOCUMENTS

| | | | |
|---|---|---|---|
| 5,578,054 | A | 11/1996 | Arnold |
| 5,613,978 | A * | 3/1997 | Harding .................. 606/181 |
| 5,662,661 | A | 9/1997 | Boudjema |
| 5,676,680 | A | 10/1997 | Lim |
| 5,693,064 | A | 12/1997 | Arnold |
| 5,707,362 | A | 1/1998 | Yoon |
| 5,725,553 | A | 3/1998 | Moenning |
| 5,766,177 | A | 6/1998 | Lucas-Dean |
| 5,792,163 | A | 8/1998 | Hitzig |
| 5,792,169 | A | 8/1998 | Markman |
| 5,817,120 | A | 10/1998 | Rassman |
| 5,827,297 | A | 10/1998 | Boudjema |
| 5,895,403 | A * | 4/1999 | Collinsworth ............ 606/184 |
| 5,922,000 | A | 7/1999 | Chodorow |
| 5,989,273 | A | 11/1999 | Arnold |
| 6,059,807 | A | 5/2000 | Boudjema |
| 6,120,521 | A | 9/2000 | Casparian |
| 6,315,737 | B1 | 11/2001 | Skinner |
| 6,461,369 | B1 | 10/2002 | Kim |
| 6,482,178 | B1 | 11/2002 | Andrews et al. |
| 6,572,625 | B1 | 6/2003 | Rassman |
| 6,579,281 | B2 | 6/2003 | Palmer et al. |
| 6,601,748 | B1 | 8/2003 | Fung |
| 6,641,564 | B1 | 11/2003 | Kraus |
| 7,172,604 | B2 | 2/2007 | Cole |
| 7,261,721 | B2 | 8/2007 | Feller |
| 8,182,493 | B2 | 5/2012 | Cole |
| 8,202,279 | B2 | 6/2012 | Cole |
| 2002/0013572 | A1 | 1/2002 | Berlin |
| 2002/0099393 | A1 | 7/2002 | Fleischman et al. |
| 2003/0040766 | A1 | 2/2003 | Werner |
| 2003/0097143 | A1 | 5/2003 | Mittelstaedt |
| 2003/0097144 | A1* | 5/2003 | Lee ......................... 606/187 |
| 2003/0120297 | A1 | 6/2003 | Beyerlein |
| 2003/0233112 | A1* | 12/2003 | Alden et al. ............ 606/181 |
| 2003/0233114 | A1 | 12/2003 | Merboth et al. |
| 2004/0193203 | A1 | 9/2004 | Pak et al. |
| 2004/0199195 | A1 | 10/2004 | Dumontelle |
| 2004/0260241 | A1 | 12/2004 | Yamamoto et al. |
| 2005/0075651 | A1 | 4/2005 | Ortiz |
| 2005/0187573 | A1 | 8/2005 | Rassman et al. |
| 2005/0267506 | A1 | 12/2005 | Harris |
| 2006/0072805 | A1 | 4/2006 | Tsipouras et al. |
| 2006/0273135 | A1 | 12/2006 | Beetel |

FOREIGN PATENT DOCUMENTS

| | | |
|---|---|---|
| WO | 98/47434 | 10/1998 |
| WO | 0110307 | 2/2001 |
| WO | 03/096906 | 11/2003 |

OTHER PUBLICATIONS

Non-final Office action mailed Apr. 19, 2005 in related U.S. Appl. No. 10/795,835, 4 pages.
Amendment filed May 18, 2005 in related U.S. Appl. No. 10/795,835, 10 pages.
Non-final Office action mailed Jul. 12, 2005 in related U.S. Appl. No. 10/795,835, 9 pages.
Amendment filed Oct. 12, 2005 in related U.S. Appl. No. 10/795,835, 4 pages.
Non-final Office action mailed Jan. 4, 2006 in related U.S. Appl. No. 10/795,835, 7 pages.
Amendment filed May 2, 2006 in related U.S. Appl. No. 10/795,835, 11 pages.
Notice of Allowance mailed Aug. 1, 2006, in related U.S. Appl. No. 10/795,835, 6 pages.
Issue Fee and Formal Drawings filed Nov. 1, 2006 in related U.S. Appl. No. 10/795,835, 8 pages.
Issue Notification mailed Jan. 17, 2007 in related U.S. Appl. No. 10/795,835, 1 page.
Certificate of Correction filed Jun. 19, 2007 in related U.S. Appl. No. 10/795,835, 2 pages.
Certificate of Correction mailed Jul. 31, 2007 in related U.S. Appl. No. 10/795,835, 1 page.
European Search Report, in related matter PCT/US2004/023533, Dated Mar. 27, 2007, 81 pages.
Preliminary Amendment filed Aug. 17, 2006 in related U.S. Appl. No. 11/506,564, 7 pages.
Second Preliminary Amendment filed Nov. 9, 2006 in related U.S. Appl. No. 11/506,564, 13 pages.
Preliminary Amendment filed Nov. 30, 2006 in related U.S. Appl. No. 11/565,553, 18 pages.
Patent Application filed Jan. 3, 2006 in related U.S. Appl. No. 11/325,388, 46 pages.
Preliminary Amendment filed Jun. 4, 2007 in related U.S. Appl. No. 11/508,669, 4 pages.
Preliminary Amendment filed Nov. 9, 2006 in related U.S. Appl. No. 11/558,338, 18 pages.
Specification filed Mar. 9, 2007 in related U.S. Appl. No. 11/558,338, 51 pages.
Restriction Requirement mailed Dec. 10, 2008 in related U.S. Appl. No. 11/558,338, 7 pages.
Patent Application filed Oct. 16, 2006 in related U.S. Appl. No. 11/549,942, 29 pages.
International Search Report and Written Opinion mailed Jul. 24, 2008, in related matter No. PCT/US07/81519, 133 pages.
Bernstein Medical Center for Hair Restoration, "Instrumentation for Three-Step FUE" 3 pages, www.bernstelnmedical.com/hair-transplant/follicular-extraction-Instrumentation.php.
Response to Restriction Requirement filed Feb. 2, 2009 in related U.S. Appl. No. 11/558,338, 12 pages.
Office action mailed Apr. 15, 2009 in co-pending U.S. Appl. No. 11/558,338, 13 pages.
Office action: Restriction Requirement mailed Apr. 1, 2009 in related U.S. Appl. No. 11/549,942, 8 pages.
Response filed Jul. 14, 2009 in co-pending U.S. Appl. No. 11/558,338, 22 pages.
Office action: Restriction Requirement mailed Jun. 3, 2009 in related U.S. Appl. No. 11/549,942, 8 pages.
Response to Restriction Requirement filed Jul. 2, 2009 in related U.S. Appl. No. 11/549,942, 11 pages.
Office action: mailed Sep. 16, 2009 in U.S. Appl. No. 11/549,942, 19 pages.
Boudjema, "The FUExtractor® System: New Instrumentation to Improve Follicular Unit Extraction", Hair Transplantation Forum International, 1 page, Sep./Oct. 2006.
Bernstein Medical Center for Hair Restoration, "Instrumentation for Three-Step FUE" 3 pages, www.bernsteinmedical.com/hair-transplant/follicular-extraction-Instrumentation.php, Jan. 2006.
Unger, et al., "Hair Transplantation", Fourth Edition, Revised and Expanded, pp. 353-354, Jan. 1, 2004.
Brandy, "New Instrumentation for Hair Transplantation Surgery", Dermatologic Surgery, Elsevier Science, New York, NY, vol. 24, No. 6, pp. 629-631, Jun. 1998.
Application as filed (U.S. Appl. No. 10/795,835, filed Mar. 9, 2004), 56 pages.
Notice to file missing parts mailed May 25, 2004 for U.S. Appl. No. 10/795,835, 2 pages.
Response to notice to file missing parts mailed Jun. 17, 2004 for U.S. Appl. No. 10/795,835, 2 pages.
Restriction Requirement mailed Apr. 19, 2005 for U.S. Appl. No. 10/795,835, 4 pages.
Response to Restriction Requirement mailed May 18, 2005 for U.S. Appl. No. 10/795,835, 11 pages.
Office Action mailed Jul. 12, 2005 for U.S. Appl. No. 10/795,835, 9 pages.
Office Action Response mailed Oct. 12, 2005 for U.S. Appl. No. 10/795,835, 12 pages.
Office Action mailed Jan. 4, 2006 for U.S. Appl. No. 10/795,835, 7 pages.
Office Action Response mailed May 2, 2006 for U.S. Appl. No. 10/795,835, 12 pages.
Notice of Allowance mailed Aug. 1, 2006 for U.S. Appl. No. 10/795,835, 8 pages.

(56) References Cited

OTHER PUBLICATIONS

Issue Fee Payment, Corrected Drawings and Comments on Statement of Reasons for Allowance mailed Nov. 1, 2006 for U.S. Appl. No. 10/795,835, 9 pages.
Request for Cetificate of Correction mailed Jun. 19, 2007 for U.S. Appl. No. 10/795,835, 5 pages.
Certificate of Correction mailed Jul. 31, 2007 for U.S. Appl. No. 10/795,835, 1 page.
Application as filed (U.S. Appl. No. 11/506,564, filed Aug. 17, 2006), 64 pages.
Notice to file missing parts mailed Sep. 5, 2006 for U.S. Appl. No. 11/506,564, 2 pages.
Response to notice to file missing parts mailed Nov. 1, 2006 for U.S. Appl. No. 11/506,564, 14 pages.
Second Preliminary Amendment mailed Nov. 9, 2006 for U.S. Appl. No. 11/506,564, 14 pages.
Filing Receipt mailed Nov. 9, 2006 for U.S. Appl. No. 11/506,564, 3 pages.
Rescission of Non-Publication Request mailed Aug. 27, 2008 for U.S. Appl. No. 11/506,564, 1 page.
Petition to Revive Application mailed Aug. 27, 2008 for U.S. Appl. No. 11/506,564, 8 pages.
Communication regarding Rescission of Non-Publication Request mailed Nov. 20, 2007 for U.S. Appl. No. 11/506,564, 4 pages.
Notice of Publication mailed Nov. 23, 2007 for U.S. Appl. No. 11/506,564, 2 pages.
Restriction Requirement mailed Dec. 8, 2009 for U.S. Appl. No. 11/506,564, 7 pages.
Response to Restriction Requirement mailed Feb. 8, 2010 for U.S. Appl. No. 11/506,564, 10 pages.
Office Action mailed Apr. 23, 2010 for U.S. Appl. No. 11/506,564, 12 pages.
Interview Summary mailed Aug. 4, 2010 for U.S. Appl. No. 11/506,564, 2 pages.
Office Action Response and Terminal Disclaimer mailed Aug. 23, 2010 for U.S. Appl. No. 11/506,564, 19 pages.
Application as filed (U.S. Appl. No. 11/565,553, filed Nov. 30, 2006), 60 pages
Notice to file missing parts mailed Sep. 5, 2006 for U.S. Appl. No. 11/565,553, 2 pages.
Filing Receipt mailed Jan. 16, 2007 for U.S. Appl. No. 11/565,553, 3 pages.
Response to notice to file missing parts mailed Jun. 1, 2007 for U.S. Appl. No. 11/565,553, 4 pages.
Updated Filing Receipt mailed Jun. 6, 2007 for U.S. Appl. No. 11/565,553, 3 pages.
Notice of Publication mailed Sep. 13, 2007 for U.S. Appl. No. 11/565,553, 1 page.
Restriction Requirement mailed Dec. 7, 2009 for U.S. Appl. No. 11/565,553, 7 pages.
Response to Restriction Requirement mailed Feb. 8, 2010 for U.S. Appl. No. 11/565,553, 18 pages.
Office Action mailed May 12, 2010 for U.S. Appl. No. 11/565,553, 18 pages.
Interview Summary mailed Aug. 4, 2010 for U.S. Appl. No. 11/565,553, 3 pages.
Office Action Response mailed Aug. 12, 2010 for U.S. Appl. No. 11/565,553, 27 pages.
Application as filed (U.S. Appl. No. 11/508,669, filed Aug. 22, 2006), 108 pages.
Notice to file missing parts mailed Sep. 8, 2006 for U.S. Appl. No. 11/508,669, 2 pages.
Response to notice to file missing parts mailed Jan. 8, 2007 for U.S. Appl. No. 11/508,669, 7 pages.
Filing Receipt and Notice of Informal Application mailed Jan. 16, 2007 for U.S. Appl. No. 11/508,669, 4 pages.
Petition under 37 C.F.R. 1.78 and Preliminary Amendment mailed Jun. 4, 2007 for U.S. Appl. No. 11/508,669, 6 pages.
Notice of Publication mailed Jul. 5, 2007 for U.S. Appl. No. 11/508,669, 1 page.
Corrected Filing Receipt mailed Aug. 9, 2007 for U.S. Appl. No. 11/508,669, 3 pages.
Decision for Petition under 37 C.F.R. 1.78 and Corrected Filing Receipt mailed Aug. 13, 2007 for U.S. Appl. No. 11/508,669, 10 pages.
Notice of Publication mailed Dec. 20, 2007 for U.S. Appl. No. 11/508,669, 1 page.
Restriction Requirement mailed Dec. 8, 2009 for U.S. Appl. No. 11/508,669, 8 pages.
Response to Restriction Requirement mailed Feb. 8, 2010 for U.S. Appl. No. 11/508,669, 20 pages.
Office Action mailed Apr. 28, 2010 for U.S. Appl. No. 11/508,669, 12 pages.
Office Action Response and Terminal Disclaimer mailed Jul. 28, 2010 for U.S. Appl. No. 11/508,669, 36 pages.
Interview Summary mailed Aug. 4, 2010 for U.S. Appl. No. 11/508,669, 4 pages.
Decision on Terminal Disclaimer mailed Sep. 1, 2010 for U.S. Appl. No. 11/508,669, 1 page.
Final Office Action mailed Oct. 26, 2010 for U.S. Appl. No. 11/508,669, 11 pages.
Application as filed (U.S. Appl. No. 11/558,338, filed Nov. 9, 2006), 55 pages.
Notice to file missing parts and filing receipt mailed Jan. 12, 2007 for U.S. Appl. No. 11/558,338, 5 pages.
Response to notice to file missing parts mailed Mar. 9, 2007 for U.S. Appl. No. 11/558,338, 56 pages.
Updated Filing Receipt mailed March 22, 2007 for U.S. Appl. No. 11/558,338, 3 pages.
Publication notice mailed Jun. 28, 2007 for U.S. Appl. No. 11/558,338, 1 page.
Restriction Requirement mailed Dec. 10, 2008 for U.S. Appl. No. 11/558,338, 7 pages.
Restriction Requirement Response mailed Feb. 2, 2009 for U.S. Appl. No. 11/558,338, 12 pages.
Office Action mailed Apr. 15, 2009 for U.S. Appl. No. 11/558,338, 7 pages.
Office Action Response mailed Jul. 14, 2009 for U.S. Appl. No. 11/558,338, 18 pages.
Office Action mailed Nov. 19, 2009 for U.S. Appl. No. 11/558,338, 9 pages.
Office Action Response mailed Feb. 18, 2010 for U.S. Appl. No. 11/558,338, 25 pages.
Final Office Action mailed Aug. 3, 2010 for U.S. Appl. No. 11/558,338, 19 pages.
Final Office Action Response mailed Oct. 4, 2010 for U.S. Appl. No. 11/558,338, 21 pages.
Advisory Action mailed Oct. 28, 2010 for U.S. Appl. No. 11/558,338, 2 pages.
Request for Continued Examination mailed Nov. 3, 2010 for U.S. Appl. No. 11/558,338, 21 pages.
Written Opinion mailed Sep. 13, 2005 for PCT/US04/023533, 3 pages.
Publication of Application mailed Oct. 13, 2005 for PCT/US04/023533, 49 pages.
Article 19 Publication mailed Dec. 29, 2005 for PCT/US04/023553, 6 pages.
Preliminary Report on Patentability for PCT/US04/023533, 4 pages.
EP Filing Documents for EP National stage mailed Oct. 9, 2006 for EP04778857.5, 7 pages.
Publication Notice mailed Nov. 15, 2006 for EP04778857.5, 1 page.
European Search Report mailed Mar. 27, 2007 for EP04778857.5, 5 pages.
Official Letter from EPO mailed Jul. 27, 2007 for EP04778857.5, 1 page.
Article 94(3) communication mailed Feb. 20, 2008 for EP04778857.5, 8 pages.
Application as field, mailed Jan. 3, 2007 for PCT/US07/060056, 68 pages.
Notification concerning Submission or Transmittal of Priority Document mailed Jun. 14, 2007 for PCT/US07/060056, 1 page.
Publication of ISR mailed Aug. 2, 2007 for PCT/US07/060056, 2 pages.

(56) References Cited

OTHER PUBLICATIONS

Entry into EP phase mailed Jun. 6, 2008 for PCT/US07/060056, 3 pages.
Written Opinion mailed Jul. 16, 2008 for PCT/US07/060056, 9 pages.
Notification Concerning Transmittal of International Preliminary Report of Patentability for PCT/US07/060056, 2 pages.
Decision on Terminal Disclaimer, mailed Sep. 19, 2010 for U.S. Appl. No. 11/506,564, 1 page.
Final Office Action, mailed Nov. 29, 2010 for U.S. Appl. No. 11/506,564, 15 pages.
Examiner's interview summary, mailed Feb. 24, 2011 for U.S. Appl. No. 11/506,564, 4 pages.
Request for continued examination and terminal disclaimer, mailed Mar. 29, 2011 for U.S. Appl. No. 11/506,564, 33 pages.
Non-Final Office Action, mailed May 23, 2011 for U.S. Appl. No. 11/506,564, 21 pages.
Final Office Action, mailed Nov. 5, 2010 for U.S. Appl. No. 11/565,553, 21 pages.
Interview Summary, mailed Jan. 10, 2011 for U.S. Appl. No. 11/565,553, 4 pages.
Request for continued examination, mailed May 5, 2011 for U.S. Appl. No. 11/565,553, 37 pages.
Interview summary, mailed Jan. 3, 2011 for U.S. Appl. No. 11/508,669, 4 pages.
Request for continued examination and terminal disclaimer, mailed Jan. 26, 2011 for U.S. Appl. No. 11/508,669, 41 pages.
Decision on Terminal Disclaimer, mailed Apr. 15, 2011 for U.S. Appl. No. 11/508,669, 3 pages.
Non-Final Office Action response, mailed Aug. 23, 2011 for U.S. Appl. No. 11/506,564, 27 pages.
Non-Final Office Action, mailed Aug. 4, 2011 for U.S. Appl. No. 11/508,669, 11 pages.
Non-Final Office Action, mailed Jun. 24, 2011 for U.S. Appl. No. 11/558,338, 19 pages.
Notice of Allowance and issue fee dues, mailed Jan. 20, 2012, for U.S. Appl. No. 11/506,564, 15 pages.
Issue fee payment, mailed Apr. 20, 2012, for U.S. Appl. No. 11/506,564, 8 pages.
Issue notification, mailed May 2, 2012, for U.S. Appl. No. 11/506,564, 1 page.
Application as filed May 14, 2012, for U.S. Appl. No. 13/471,307, 66 pages.
Filing receipt and notice to file missing parts, mailed May 25, 2012, for U.S. Appl. No. 13/471,307, 6 pages.
Applicant response to notice to file missing parts, mailed Jul. 25, 2012 for U.S. Appl. No. 13/471,307, 71 pages.
Updated filing receipt, mailed Aug. 10, 2012, for U.S. Appl. No. 13/471,307, 4 pages.
Non-Final Office Action Response mailed Jan. 4, 2012 for U.S. Appl. No. 11/508,669, 38 pages.
Final Office Action, mailed Mar. 14, 2012 for U.S. Appl. No. 11/508,669, 14 pages.
Request for Continued examination, mailed Aug. 14, 2012, for U.S. Appl. No. 11/508,669, 50 pages.
Notice of Allowance mailed Dec. 23, 2011 for U.S. Appl. No. 11/558,338, 8 pages.
Issue Fee payment, mailed Mar. 23, 2012, for U.S. Appl. 11/558,338, 13 pages.
Issue Notification, mailed May 30, 2012, for U.S. Appl. No. 11/558,338, 1 page.
Application as filed Apr. 16, 2012, for U.S. Appl. No. 13/448,232, 65 pages.
Filing receipt and notice to file missing parts, mailed May 2, 2012, for U.S. Appl. No. 13/448,232, 6 pages.
Applicant response to notice to file missing parts, mailed Jul. 2, 2012 for U.S. Appl. No. 13/448,232, 68 pages.
Updated filing receipt, mailed Jul. 12, 2012, for U.S. Appl. No. 13/448,232, 5 pages.

* cited by examiner

ENHANCED FOLLICULAR EXTRACTION PUNCH AND METHOD

RELATED APPLICATIONS

This application is a continuation-in-part of U.S. patent application Ser. No. 10/795,835 filed on Mar. 9, 2004 titled, "Follicular Extraction Device and Method" by John P. Cole, now U.S. Pat. No. 7,172,604.

BACKGROUND

1. Field

This disclosure relates to surgical instruments and method used for extracting hair follicles.

2. Background Information

In hair transplantation procedures, hair is typically extracted from the scalp of a subject in one area of the scalp, referred to as a "donor" region, and is then implanted in another area, referred to as a "recipient" region. These procedures are typically time-consuming and require considerable specialized expertise because of the minute dimensions of individual hair follicles, the large number of individual follicles involved in a given transplantation, variability in the depth of hair follicles, the fragility of hair follicles, and the variation in dermal characteristics upon which the procedure is performed. Hairs typically grow in clusters consisting of one to six or more hairs. These clusters are termed follicular clusters, follicular groups, or follicular units. Each individual follicle within a follicular cluster is surrounded by a membrane termed a hair follicle sheath. The hair follicle sheath surrounds a hair shaft and extends from the upper dermis to the subcutaneous fat.

Hairs in the donor region are traditionally extracted by employing a sharp scalpel to excise a large section of the scalp that may be more than 1 cm wide and over 30 cm long from the donor region. This process is called strip donor harvesting. Strip donor harvesting results in a linear scar that may range between 0.1 mm to over 1 cm in width and may be over 30 cm long. The average strip scar is between 2 mm and 5 mm wide and its width may vary along the length of the strip scar. Linear strip scars create difficulties in concealment in many instances especially with short hair styles. Furthermore, strip harvests contain thousands of individual follicular clusters that must be further subdivided into individual follicular clusters. This is a time consuming process with a high rate of injury to the individual follicles. This injury results in waste of a finite supply of hair.

DETAILED DESCRIPTION

In the following detailed description, numerous specific details are set forth in order to provide a thorough understanding of claimed subject matter. However, it will be understood by those skilled in the art that claimed subject matter may be practiced without these specific details. In other instances, well-known methods, procedures, and components have not been described in detail so as not to obscure claimed subject matter.

Figure 1A:
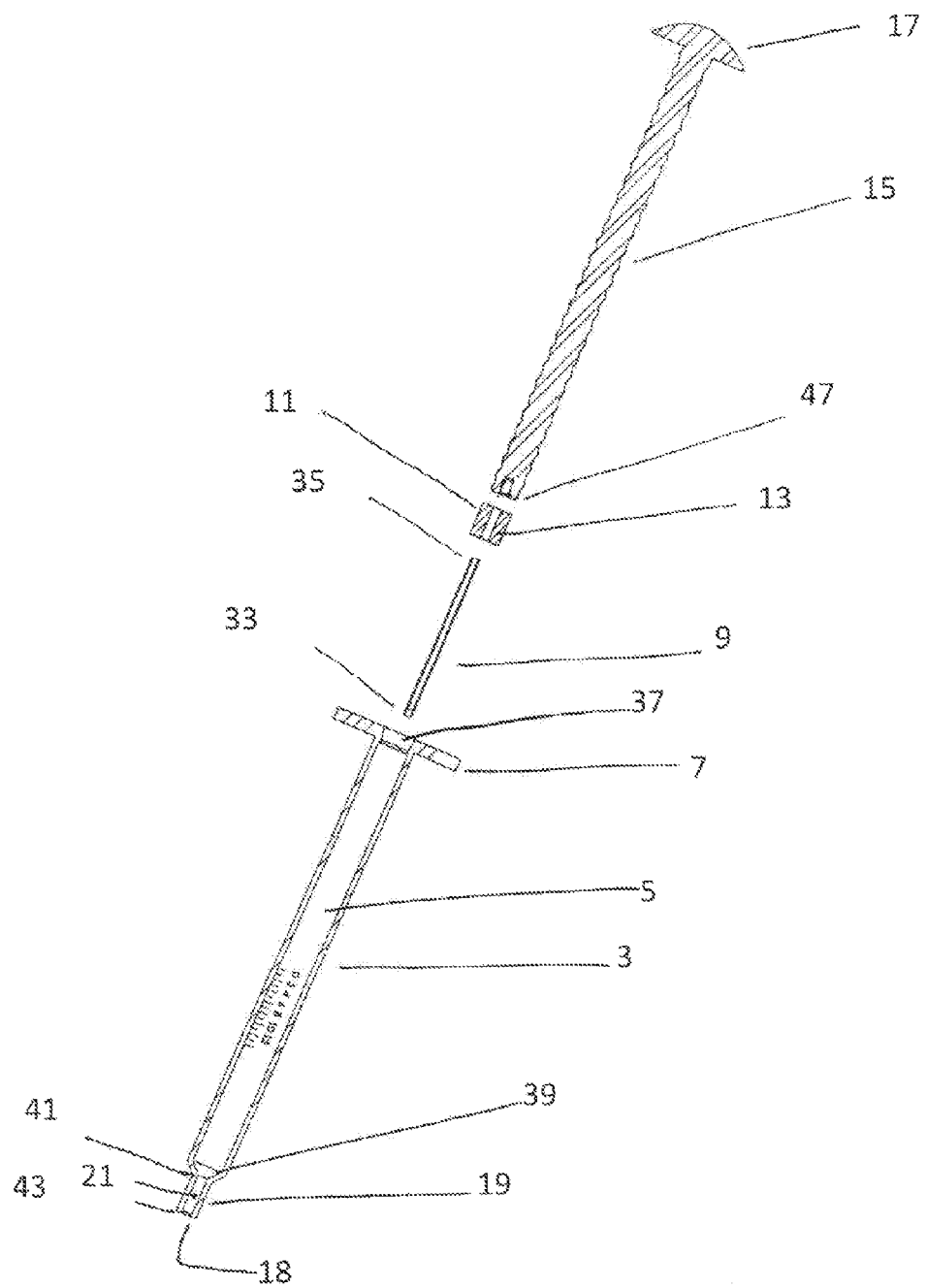
FIG. 1a is an exploded view of an extraction instrument according to an embodiment.

FIG. 1a illustrates an embodiment of an instrument for extracting hair follicles. The instrument includes main body portion 3, a punch 9, a stabilizer 11, and an actuator 15 to control positioning and depth of punch 9, implemented in the depicted embodiment as actuator 15, a screw. It should be understood, however, that a screw is merely an example of an actuator for use in positioning and controlling the depth of a punch according to a particular embodiment, and claimed subjected matter is not limited in this respect. Main body portion 3 may take a variety of forms and shapes, including, for example, a cylinder (as illustrated), or a rectangular prism. However, these are merely examples of shapes that may be used to form a body of a hair extraction instrument. Main body portion 3 includes an open first end portion 37, a second end portion 39 and a main bore 5 centrally disposed between the first 37 and second 39 end portions, which may, in a given embodiment, extend the length of main body portion 3 from the first to the second end portion. The walls of main body portion 3 toward the second end portion 39 may be cylindrical or tapered inwards towards the axis of the main bore 5 and may coextensively intersect a nipple end portion 19 ("nipple end") which further includes a first end portion 41 and a tip portion 43. Nipple end 19 may also take a variety of shapes such as, for example, substantially cylindrical, or tapered shapes to name a few. The second end portion 39 of main body portion 3 may be attached to nipple end 19 via the first end portion 41 of nipple end 19. Nipple end 19 includes a bore 21 disposed along its longest dimension which extends from the first end portion 41 to the tip portion 43. Thus, bore of nipple end 19 may be directly coupled to the main bore 5 of main body portion 3. Additionally, the main bore 5 may be exposed to ambient surroundings at the first end portion 37, while bore 21 of nipple end 19 may be similarly exposed at tip portion 43.

According to a particular embodiment, main body portion 3 and nipple end 19 may be assembled from two or more pieces or formed integrally together by, for example, an injection molding process using a plastic material. However, this is merely an example of how a main body portion and nipple end may be formed according to a particular embodiment and claimed subject matter is not so limited. In the particularly illustrated embodiment, punch 9 has two ends, first end portion 35 and sharp or cutting end portion 33. Additionally, punch 9 may have a substantially cylindrical shape and may have a flat cutting edge (not shown). Additionally, punch 9 may be made of a variety of materials such as stainless steel, titanium, or other metal alloy, for example. However, these are merely particular examples of materials that can be used to form a punch and claimed subject matter is not so limited.

Nipple end 19 may be of varied lengths. For example, the length of nipple end 19 may be between 2 and 25 millimeters, such as, for example, 6 millimeters. Lip portion 18 may be formed at the tip of the nipple end providing stabilization of the device with respect to the skin (not shown). Lip portion 18 may also provide control of the depth of incision of punch 9 by preventing punch 9 from penetrating the skin of the patient beyond the desired depth. Here, accordingly, the depth that punch 9 penetrates in the skin of the patient may be limited to the extent to which punch 9 extends out of the nipple beyond lip portion 18. Lip portion 18 comprises a surface that is closely coupled to punch 9 which abuts the skin to thereby limit the depth that punch 9 may extend beyond the surface of the skin. Adjusting the extent to which punch 9 extends beyond lip portion enables limiting the extension of punch 9 into the skin to a predetermined depth. However this is merely an example of a surface capable of limiting the extension of a punch into the skin to a predetermined depth and claimed subject matter is not so limited.

Bore 21 may be formed so that it is slightly smaller than an outside diameter of punch 9, to enable a snug fitting between bore 21 and punch 9 with some deformation of bore 21. Additionally, such a fit may preclude punch 9 from extraneous motions which may be caused, for example, by the surgeon handling the instrument, or by the force of gravity. According to a particular embodiment, nipple end 19 may be fabricated using a polymer such as polyolefin, and bore 43 of nipple end 19 may be at least 0.1 millimeter smaller than the outside diameter of punch 9. Again, these are merely examples of how a main body and a nipple end of an instrument may be formed and claimed subject matter is not limited in this respect.

Main body portion 3 may comprise a translucent material, including, for example, a thermoplastic polyolefin such as homopolymers of polypropylene or polyethylene, copolymers of the foregoing with any $C_{1-6}$ olefinic monomer, as such materials are well known to those in the polymer arts. However, other materials of construction including glass, various metals such as stainless steels, etc., are also suitable materials from which main body portion 3 may be constructed, and claimed subject matter is not limited in this respect. Main body portion 3 may include graduation scale markings on its outer surface to assist in setting the depth of punch 9 as explained further below. Main body portion 3 may also include a plurality of grips 7 disposed at the first end portion 37. Grips 7 may, for example, comprise flanges which extend perpendicularly with respect to the axis of bore 5. In a particular embodiment, some part of bore 5, closer to end 37 may have a diameter smaller than the actuator outer diameter in order to have threaded coupling of the two.

Figure 1B:
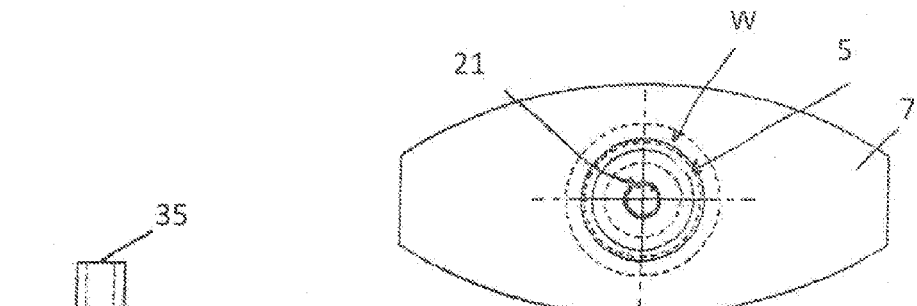
FIG. 1b is a top view of the main body portion of an extraction instrument according to an embodiment.

FIG. 1*b* illustrates a top view of a main body portion 3, according to a particular embodiment, as viewed from the first end portion 37 looking into bore 5. This view shows the respective locations of grips 7, bore 5, the thickness W of the wall portion of main body portion itself, according to a particular embodiment, and bore 21 of nipple end 19 at the far end of bore 5.

Figure 1C:
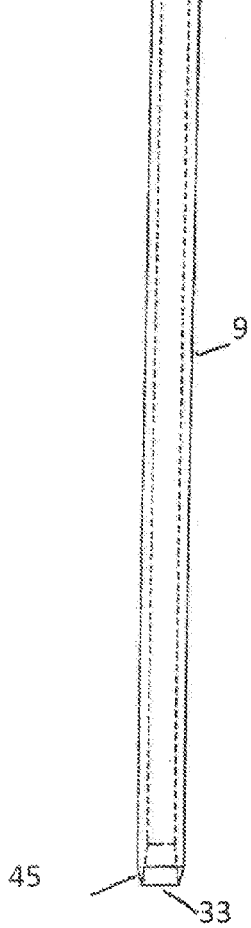
FIG. 1c is a diagram of a punch according to an embodiment.

FIG. 1*c* illustrates a view of an embodiment of a punch 9 used to assist in hair follicle extraction. Punch 9 may comprise a hollow tube and may be constructed of any number of materials such as, for example, a metal or metal alloy including stainless steel or titanium, to name a few. Protective coatings, such as titanium or zirconium, to name a few, may be applied to the surface of punch 9. Punch 9 includes a first end portion 35 and a sharp or cutting end portion 33. The sharp end portion 33 may include a beveled or angled cutting edge 45. In one particular embodiment, punch 9 comprises a hollow tube having an open top portion, an open bottom portion, and a wall portion, with a bore disposed longitudinally throughout. The inside diameter of punch 9 may be any diameter in the range between about 0.5 millimeters to about 4.5 millimeters. The outside diameter of punch 9 may be between about 0.2-0.3 millimeters larger than the inside diameter, for example. However, these are merely examples of dimensions for a punch and claimed subject matter is not limited in this respect.

Figure 1D:
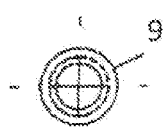
FIG. 1d is an end view of punch as illustrated in FIG. 1c according to an embodiment.
Figure 1E:
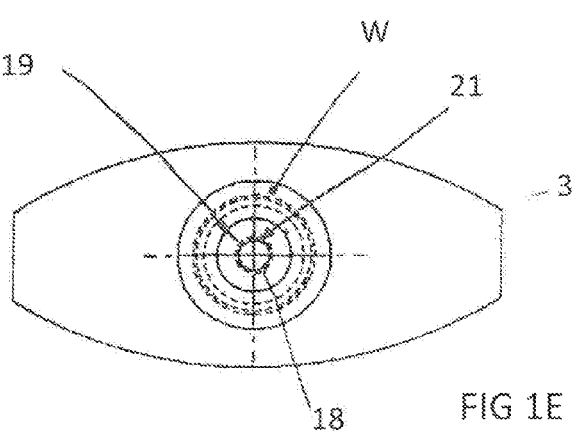
FIG. 1e is an end view of a main body portion of an extraction instrument as viewed from a nipple end according to an embodiment.

FIG. 1*d* illustrates an end view of an embodiment of punch 9, and FIG. 1*e* shows an end view of main body portion 3 as viewed from nipple end 19. The thickness of wall portion W of main body portion 3 is also shown. In FIG. 1*e*, it may be discerned that a portion of nipple end 19 comprises a lip portion 18 adapted to touch and/or abut the skin of a patient. The area of lip portion 18 which contacts and/or abuts the skin depends upon the dimensions of the wall, and the diameter of bore 21 and nipple end 19. Lip portion 18 may aid controlling the depth that punch 9 may penetrate into skin according to an embodiment.

Figure 1F:
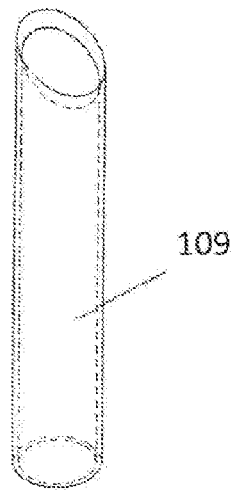
FIG. 1f shows a view of a punch according to an embodiment.
Figure 1G:
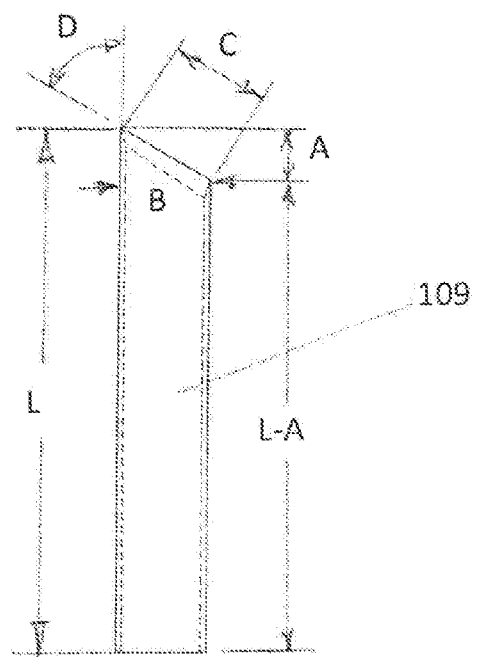
FIG. 1g shows a side view of a punch according to an embodiment.

FIG. 1*f* illustrates an isometric view of a punch 109, according to an embodiment. In a particular embodiment, punch 109 may have an angled cutting edge to facilitate an incision with a uniform initial contact between the cutting edge and the skin of a patient during follicular extraction. The angle of the cutting edge may substantially correspond to the angle of growth of a hair follicle relative to the surface of the skin. An angled punch 109 may allow a surgeon to make an incision into the skin of a patient applying pressure evenly about the hair follicle to be removed which may decrease the possibility of deforming the hair follicle prior to extraction. Reducing the risk of deformation of the hair follicle may substantially decrease the risk of shearing of the hair follicle during the follicular extraction. As illustrated in FIG. 1*g*, A (the longitudinal length of the angled cutting edge) may be about 0.58 millimeters, B (the diameter of cutting edge) is about 1 millimeter, C (the length across the angled cutting edge) is about 1.15 millimeters and the angle theta (θ) is about 60 degrees, according to a particular embodiment. However, this example is merely illustrative, and the angle theta may take a variety of acute values, such as from 30 to 90 degrees.

Referring again to FIG. 1a, a stabilizer 11 may also be included in various embodiments. Stabilizer 11 may be implemented using, for example, a cylindrical component made from an elastomeric material, such as a molded rubber. Stabilizer 11 may have an outside diameter that is approximately equal to and/or slightly greater than the diameter of main bore 5. This may enable stabilizer 11 to reside within bore 5 in a sufficiently snug manner so as to be retained within bore 5 even if main body 3 is moved or inverted and stabilizer 11 is subject to gravitational forces, for example. Additionally, stabilizer 11 may include a bore 13 having an axis that substantially coincides with an axis of stabilizer 11. Bore 13 may be slightly smaller than the outer diameter of punch 9, so as to enable first end portion 35 of punch 9 to be retained within bore 13 of stabilizer 11 by a snug interference fit induced by the slight expansion of the elastomeric material of stabilizer 11 from the insertion of punch 9 into bore 13. Stabilizer 11 may limit movement of punch 9 in a lateral direction within main bore 5, and may maintain proper alignment of punch 9 with an angle and direction of hair growth. According to a particular embodiment, polymeric material of stabilizer 11 may comprise one or more of the following: polyolefin homopolymers, such as polypropylene or polyethylene; polyolefin copolymers, including ethylene-propylene copolymers, propylene butane copolymers, and propylene-octene copolymers, thermoplastic vulcanizates and elastomers, to name a few.

Figure 2A:
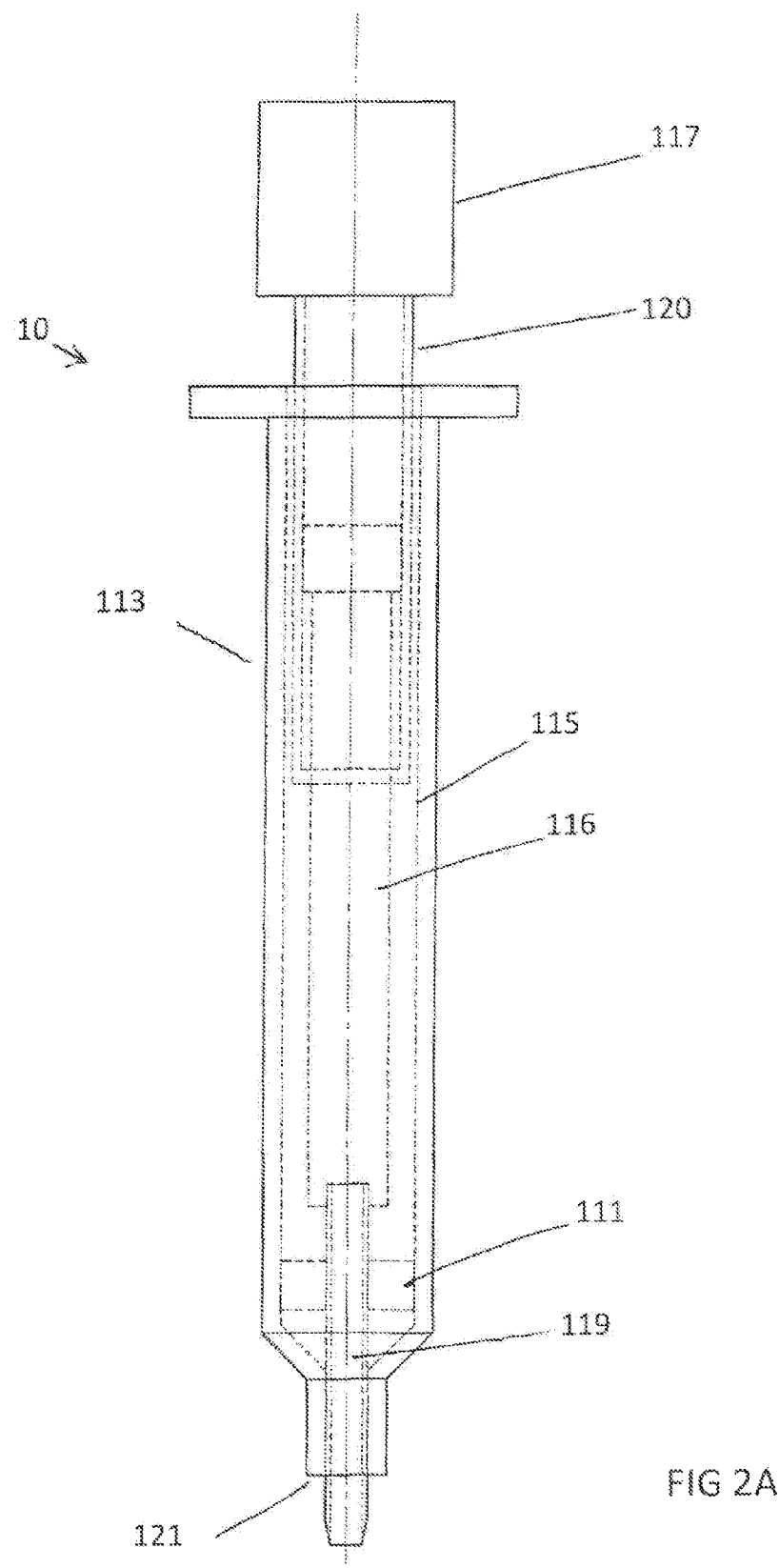
FIG. 2a is a diagram of an extraction instrument in assembled form according to an embodiment.

FIG. 2a illustrates a punch 119 coupled with a telescoping part 116 which is operated by an actuator 120. Actuator 120 may comprise, for example, a device wherein a mechanical, hydraulic, pneumatic or electromotive force acts upon actuator 120 in order to cause translation. For instance, a hydraulic or pneumatic fluid may act on the two sides of the head of the telescoping part situated in the chamber (not shown) of the actuator 120. The differential fluid pressure on the two sides of the head will enable the translation of the telescoping part in either direction. A hydraulic or pneumatic circuitry or a mechanical or an electromechanical or an electromagnetic drive (not shown) may be located near the actuator head 117 of actuator 120 and coupled to a drive system (not shown) capable of mechanizing the translation of telescoping part 116. However, there are numerous methods of automating translation of actuator system 116 and 120 and claimed subject matter is not limited in this respect.

Additionally, actuator 120 may comprise, for example, materials such as plastic or metallic material. However, these are merely examples of actuators and claimed subject matter is not limited in this respect. In this particular embodiment actuator 120 comprises a first cylinder, which is coupled to the inner surface of main bore 115 of main body portion 113 for instance by threaded connection and further comprising a telescoping portion 116 which may be a second cylinder positioned and slidably disposed within the first cylinder. In this particular embodiment, the inner surface of main bore 115 is substantially in contact with the outer surface of actuator 120 which may, for example, provide tuning adjustment of the punch depth obtained by rotating actuator 120. Head portion 117 may be in communication with the actuator 120 and/or telescoping portion 116 to enable a controlled translational extension or protraction of telescoping portion 116 in a longitudinal direction at a controlled depth. Punch 119 may be substantially in contact with telescoping portion 116 and may protrude or retract with the translational movement of activating portion 116. Lip portion 121 may contact and/or abut the skin of a patient during a follicular extraction procedure and acts as a barrier preventing punch 119 from entering the skin (not shown) of a patient during an extraction procedure beyond the distance that punch 119 protrudes beyond lip portion 121. Accordingly, lip portion 121 comprises a surface that is closely coupled to punch 119 which abuts the skin to thereby limit the depth that punch 119 may extend beyond the surface of the skin. Adjusting the extent to which punch 119 extends beyond lip portion enables limiting the extension of punch 119 into the skin to a predetermined depth. However this is merely an example of a surface capable of limiting the extension of a punch into the skin to a predetermined depth and claimed subject matter is not so limited. Stabilizer 111 may also be in contact with both the activating portion 116 and punch 119 providing additional stability to punch 119.

FIG. 1a illustrates an actuator 15 comprising a screw. In this particular embodiment, actuator 15 has a 1 mm pitch such that one full rotation results in 1 mm entrance of actuator 15 into bore 5. However, this is merely an example of screw pitch enabling a proportional axial translation of an actuator according to a particular embodiment, and claimed subject matter is not limited in this respect. Additionally, actuator 15 includes threads on its outer surface that are of such dimension as to allow them to mate with the inner surface of main bore 5 of body portion 3. In this particular embodiment main bore 5 is also threaded. However, in a different embodiment the inner wall of main bore 5 may not include threads. Where main bore 5 does not have threads, actuator 15 may be inserted into main bore 5 and threaded to a desired depth or location within main bore 5. Actuator 15 may additionally include head portion 17. Actuator 15 may be coated with an adhesive or tape to reduce slippage with respect to main bore 5.

Figure 2B:
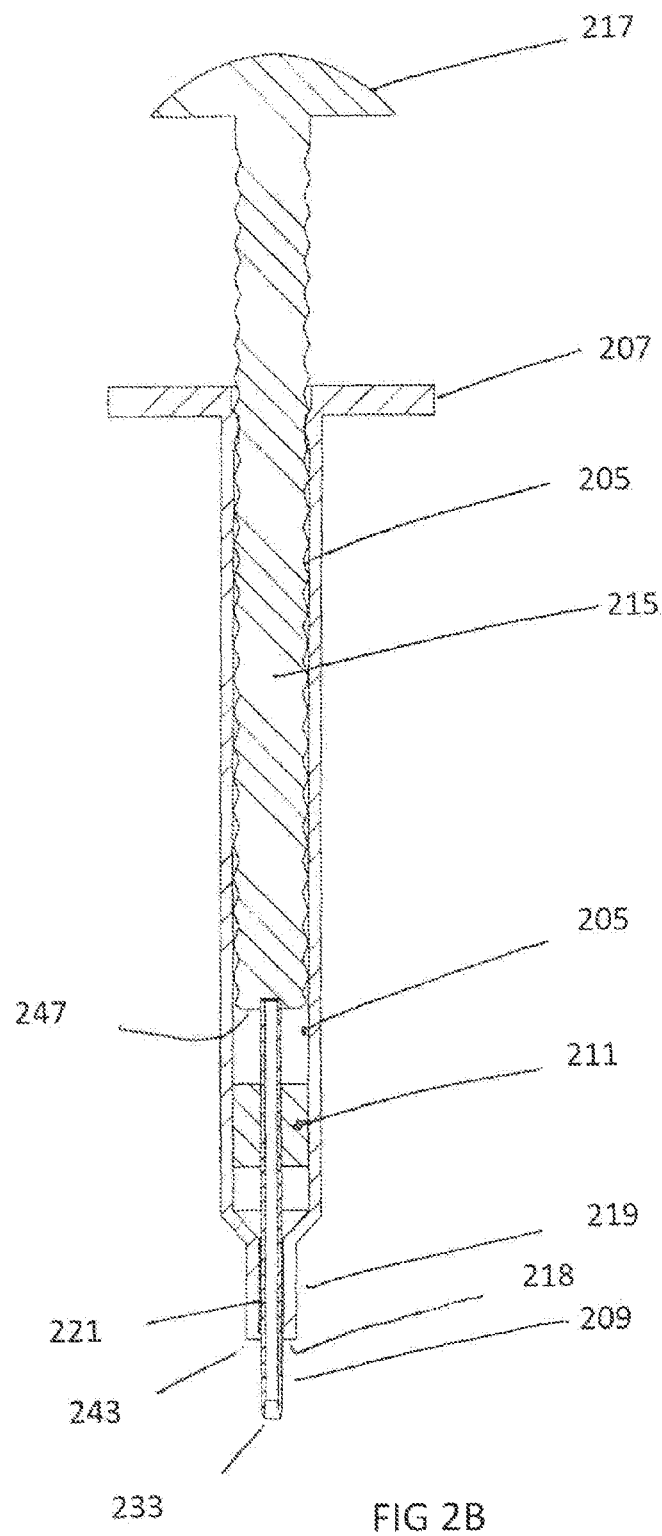
FIG. 2b is a section view of an extraction instrument in assembled form according to an embodiment.

FIG. 2b illustrates an embodiment of an assembled instrument for extracting hair follicles. As shown, punch 209 is disposed within bore 221 of nipple end 219, the inner diameter of which is equal to or slightly larger than the outer diameter of punch 209. Thus, nipple end 219 may act as a bearing for movement of punch 209 laterally within bore 221. In a particular embodiment, punch 209 may be assembled to the hole disposed in end 247 of actuator 215 by means of adhesive like epoxy or mechanically by friction or use of set screw on the side (not shown). Lip portion 218 may contact and/or abut the skin of a patient during the follicular extraction process and therefore aid in controlling the depth of the incision of punch 209. As illustrated above, such a depth of the incision of punch 209 may be limited by the extent to which punch 209 extends beyond lip portion 218. Stabilizer 211 is shown disposed between the first end portion of punch 209 and nipple end 219. In this particular embodiment, the depth of sharp cutting end 233 of punch 209, as it protrudes from tip portion of nipple end 243, may be controlled by adjustment of actuator 215, which may be a screw, within main bore 205. It is to be understood that other methods and/or components besides a screw may be used to control or affect the depth of the sharp or cutting edge of punch 209 within the extraction instrument as mentioned above and that the embodiment depicted is not to be taken as limiting claimed subject matter in any way. For example, as illustrated above, an actuator may be something other than a screw. For instance, an actuator may be a mechanical component such as a bolt, and/or pneumatic or electronic actuators, such as an actuator comprising a piezoelectric element. An actuator may selectively control the depth of the sharp or cutting end of punch 209.

Figure 3:
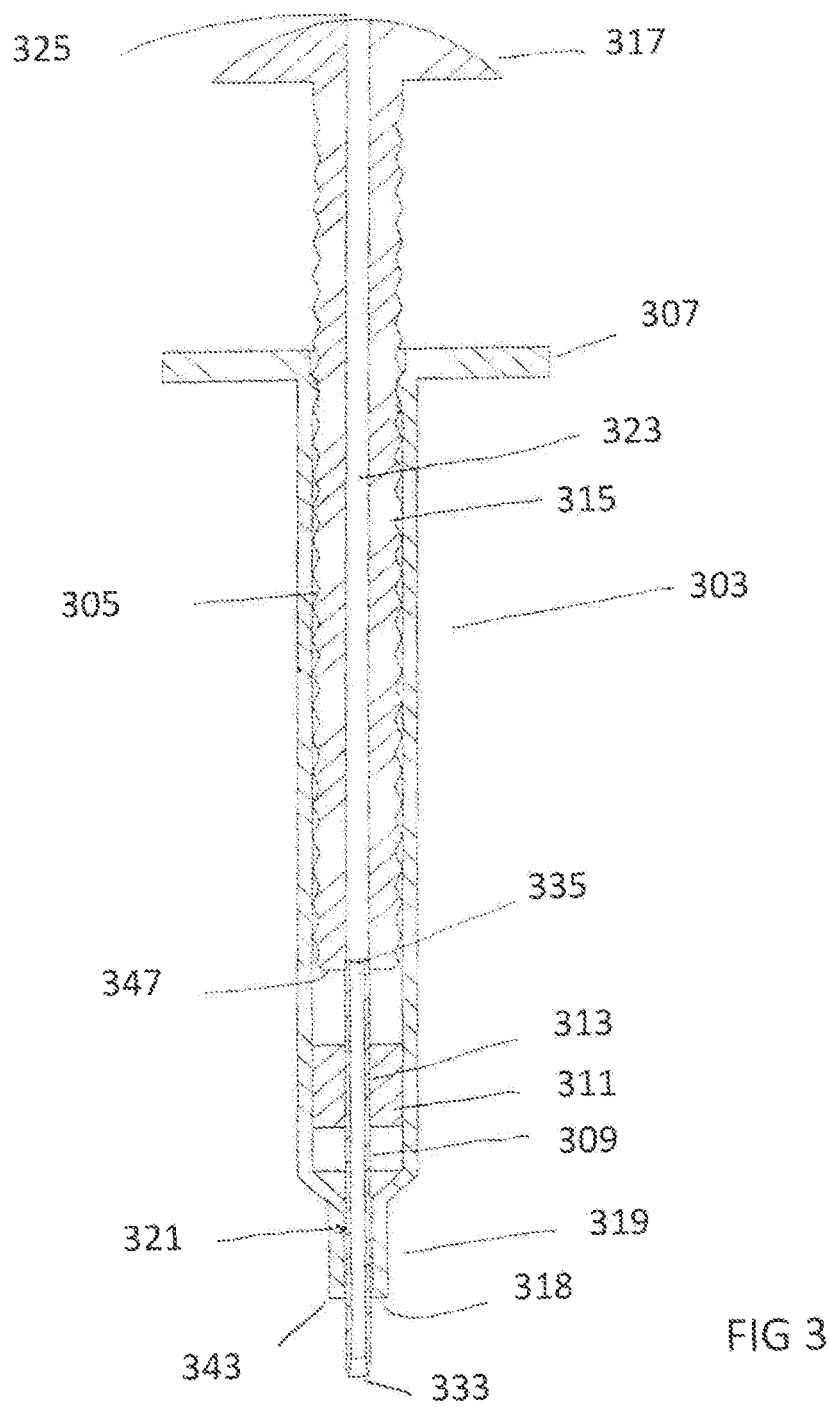
FIG. 3 is a section view of an extraction instrument in assembled form according to an embodiment.

FIG. 3 illustrates another embodiment of an assembled instrument for extracting hair follicles. In this embodiment, actuator 315 includes a bore 323 disposed along its entire length with a hole 325 at head portion 317. Head portion 317 may take on a variety of shapes, dimensions and surface coatings without departing from claimed subject matter. For example, the diameter of the head portion may be between 3-15 millimeters. Punch 309 is disposed within bore 321, similarly to FIG. 2b. Nipple end 319 may act as a guide for movement in bore 323. Stabilizer 311, disposed between first end portion of punch 309 and nipple end 319, includes a bore 313, which receives a section of punch 309. The interior of punch 309 is exposed to the hollow interior space within bore 323. Due to this exposure, there is an open passageway from the hole in the head portion of actuator 315 to the tip of punch 309. This open passageway allows various external devices to be coupled to the current device and have direct exposure to the hair follicle. For example, a suction pressure may be applied to draw a follicle, blood, fluid or serum through the instrument via a vacuum source (not shown) applied at hole 325. Similarly, an optical fiber (not shown) may be fitted through the passageway to enable the application of laser radiation to the follicle. Additionally, medicaments useful in treating and/or extracting a follicle may be applied to by eluting them through the open passageway through to the follicle. In this embodiment, similarly to that shown in FIG. 2, the adjustment of an actuator 315 is used to control the depth of sharp end 333 of punch 309.

Referring again to FIG. 1a, the assembly of the depicted follicle extraction instruments may be performed as follows. First, main body portion 3 may be provided. Next, punch 9 and stabilizer 11 are placed within bores 21 and 5, respectively. Punch 9 may be placed into bore 21 first, and then separately placing stabilizer 11 into an opening at first end portion 37 of main body portion 3 and forcing it downwards (such as with a rigid object such as a pencil, screwdriver, etc.) into bore 5 until stabilizer 11 comes into contact with punch 9. Alternatively, stabilizer 11 may itself include a bore 13 into which an end of punch 9 is first partially inserted, forming a sub-assembly including punch 9 and stabilizer 11. This sub-assembly may then be placed into an opening at first end portion 37 of main body portion 3 with punch 9 of the sub-assembly being inserted first, taking care that punch 9 enters bore 13 as the sub-assembly approaches second end portion 39 of main body 3. Subsequent to the placement of punch 9 and stabilizer 11 at their respective locations within main body portion 3, actuator 15 may be placed into bore 5, which may be accomplished by turning actuator head 17 and rotating actuator 15. Actuator 15 may enter bore 5 at a depth at which it just contacts stabilizer 11, and then actuator 15 may be advanced into bore 5, which forces the sharp end of punch 9 toward the distal end of nipple end 19. The distance that end portion of punch 9 protrudes from the end of nipple end 39 may be adjusted. As illustrated in FIG. 3, for example, by turning actuator head 317, punch 309 may be extended out of nipple end 319 by a controllable amount thus providing precise control of the depth of the incision of punch 309. Lip portion 318 may contact and/or abut the skin of a patient during the follicular extraction process and therefore aid in controlling the depth of the incision of punch 309. Various devices and techniques may be used in the context to control the protrusion distance of punch 309, as illustrated above. Referring again to FIG. 1a, according to one implementation, graduation marks, or a similar imprinted scale, may be disposed along the translucent main body to assist in controlling the protrusion distance as a guide. The graduation scale marks, may be placed on main body portion 3 using any number of techniques well known in the art.

Referring again to FIG. 3, stabilizer 311 is shown within bore 305, it is to be understood that stabilizer 311 may also be disposed in a stationary position within bore 305, or at any location within bore 305. In the current embodiment, stabilizer 311 is placed within bore 305 near nipple end portion 319. In addition, punch 309 may be slidably disposed with respect to stabilizer 311, in one embodiment, punch 309 may move with respect to stabilizer 311, for example, by motion through bore 313. In another embodiment, punch 309 may be stationary with respect to stabilizer 311, such as when stabilizer is not fixed in a stationary position within bore 305. In other embodiments, in which the main body portion 303 includes a translucent material, the user may be able to view the end 347 of the actuator within bore 305. FIG. 3 also illustrates the first end portion 335 of punch 309 assembled in front end of bore 323 of actuator 315. In one embodiment, the diameter of bore 323 through actuator 315 may be larger than the outer diameter of punch 309. In another embodiment, the diameter of bore 323 through actuator 315 may be smaller than the outer diameter of punch 309. In still another embodiment, the diameters of bore 323 and punch 309 may be substantially equivalent. In a particular embodiment, the diameter at the tip of bore 323 of actuator 315 may be adjusted to allow punch assembly. Punch 309 may protrude from stabilizer 311, so that stabilizer provides a gasket-like tight seal between the inner space within punch 309 and bore 323. End portion 335 of punch 309 may be disposed within bore 323 where the two are fixedly coupled by appropriate means as described before.

FIGS. 4-8 illustrate a follicular extraction method using a particular embodiment of an extraction device wherein the surgeon makes a first incision to a particular depth at an angle $\alpha_1$ and a second incision to a particular depth at an angle $\alpha_2$.

Figure 4:
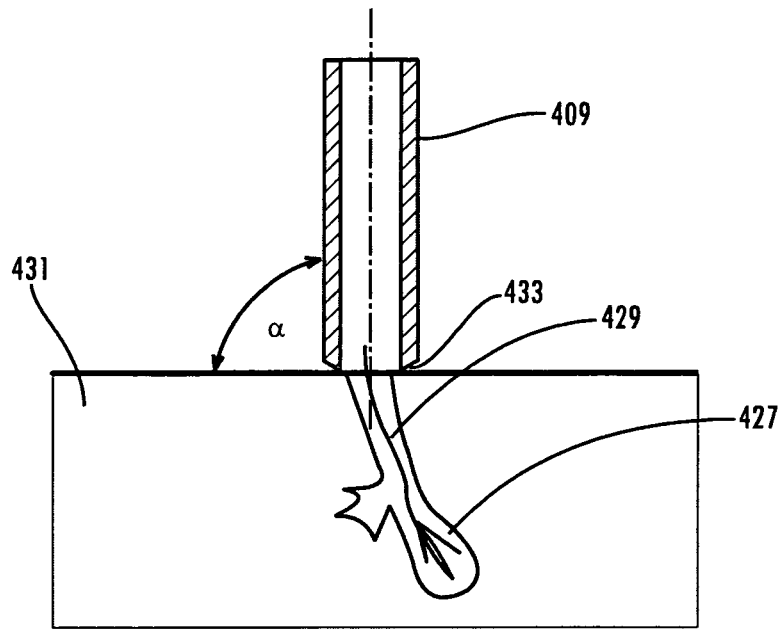
FIG. 4 is a sectional view of skin containing a hair follicle in contact with a portion of a punch according to an embodiment.

FIG. 4 shows a section of skin 431 containing a hair follicle sheath 427 with a hair shaft 429 disposed therein, wherein the surface of the skin is in contact with sharp or cutting end portion 433 of punch 409. FIG. 4 illustrates part of a process for extracting a live hair follicle from the skin using an extraction instrument as described above. In this process, punch 409 may be forced through nipple end (not shown) by an amount controlled, for instance, by an actuator (not shown). Punch 409 may initially contact the skin substantially perpendicularly to the skin surface, while the hair enters into bore of punch 409.

Figure 5:
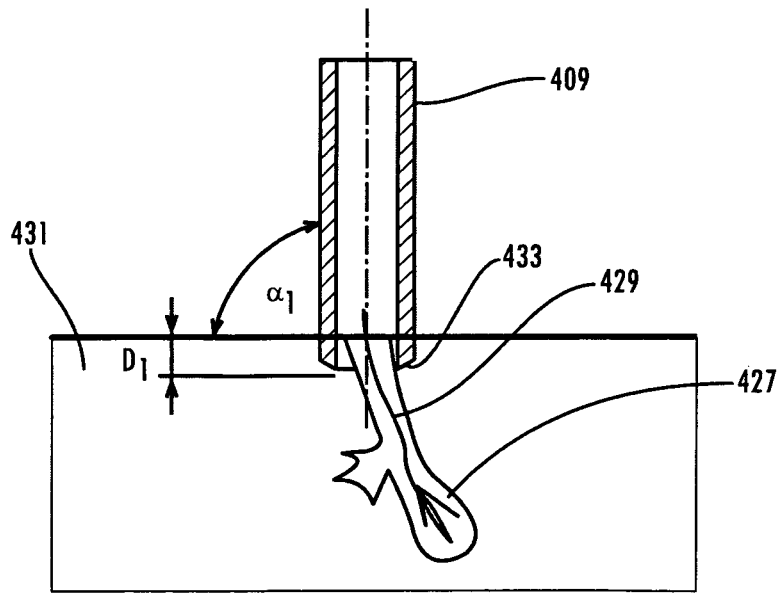
FIG. 5 is a sectional view of skin containing a hair follicle in contact with a portion of a punch extending further into the skin according to an embodiment.

As illustrated in FIG. 5, sharp or cutting end portion 433 of punch 409 may penetrate skin 431 over the location at which a hair shaft 429 is growing, by a distance denoted $D_1$, while angle $\alpha_1$ of punch 409 with respect to the skin surface may be maintained. For example, $\alpha_1$ may be maintained in a range of about 80 to 100 degrees, depending, however, on the angle of hair follicle sheath 427. Scoring or the initial penetration of punch 409 into the upper dermis of the skin of the patient is maintained at angle $\alpha_1$ and depth $D_1$ to give the surgeon control over the location of the insertion into skin 431. In addition, scoring or initial penetration may reduce the surface area of the incision so that the resulting wound is circular rather than elliptical and has the smallest circumference and the lowest probability of noticeable scarring.

Figure 6:
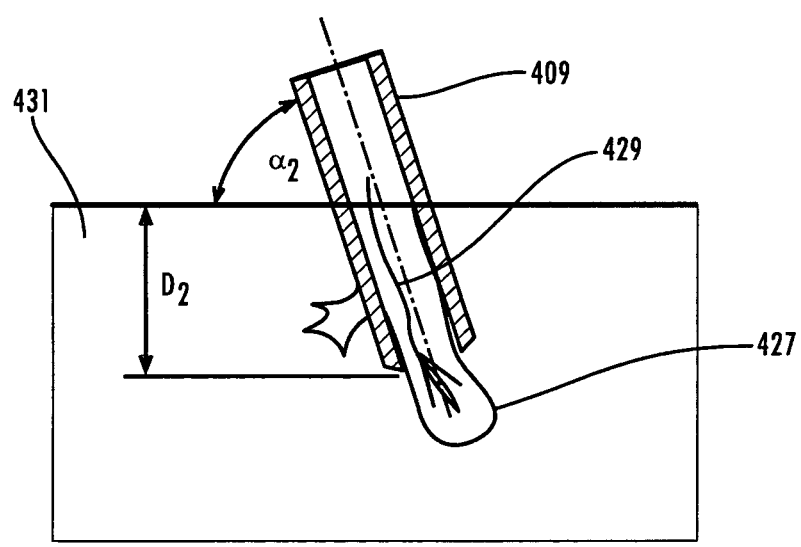
FIG. 6 shows a section of skin containing a hair follicle in contact with a portion of a punch as the instrument extends further into the skin according to an embodiment.

Referring now to FIG. 6, punch 409 may be adjusted in angle to $\alpha_2$ as it penetrates into the deeper dermis and upper subcutaneous fat to a second depth $D_2$ so as to follow the angle of the hair follicle. The initial depth, $D_1$, may be, for example, between 0.05 millimeters and 0.5 millimeters (but may be up to 1 mm deep), depending on the depth and surface characteristics of skin 431 of the patient. As punch 409 penetrates from depth $D_1$ to $D_2$, the angle $\alpha_2$ may be substantially maintained. Follicular clusters, follicular groups, or follicular units that include more than one hair may have a splaying or widening of the distance between the hairs as they enter the skin surface. This distance may become wider or more varied at greater depths in the dermis. Thus, for such clusters, it may be useful to limit the depth of the insertion, increase the diameter of the punch, or to both limit the depth and increase the diameter of the punch.

The insertion of punch 409 into the skin may be performed, according to one implementation, by applying a pressure to the follicle extraction device and cutting by such pressure through the skin. In another implementation, the follicle extraction device may be rotated (uni-directionally, bi-directional or in an oscillating manner) while under slight pressure during the insertion. Depth $D_2$, which depends on the length of the hair follicle, may range from between about 1 to about 7 millimeters, with a typical depth being about 3.8 millimeters. Once depth $D_2$ has been reached, hair follicle sheath 427 may be removed by gently tugging on the top of hair follicle sheath 427 so that hair follicle sheath 427 is removed in its entirety or a group of follicles referred to as a follicular cluster is teased out, by, for example, a pair of forceps. In addition, removal of hair follicle sheaths 427 and/or follicular clusters may be assisted by, for example, application of vacuum pressure to hole 425.

Accurate control of the depth may enable substantial removal of hair follicles and avoidance of follicular damage. While there is variance amongst individuals within any mammalian species with respect to the average depth of hair follicles and dermal papillae below the skin surface, once an average depth of follicles for a particular individual is determined, the depth $D_2$ may be set at this level, which allows a high degree of accuracy and speed in the follicle removal process.

Figure 7:
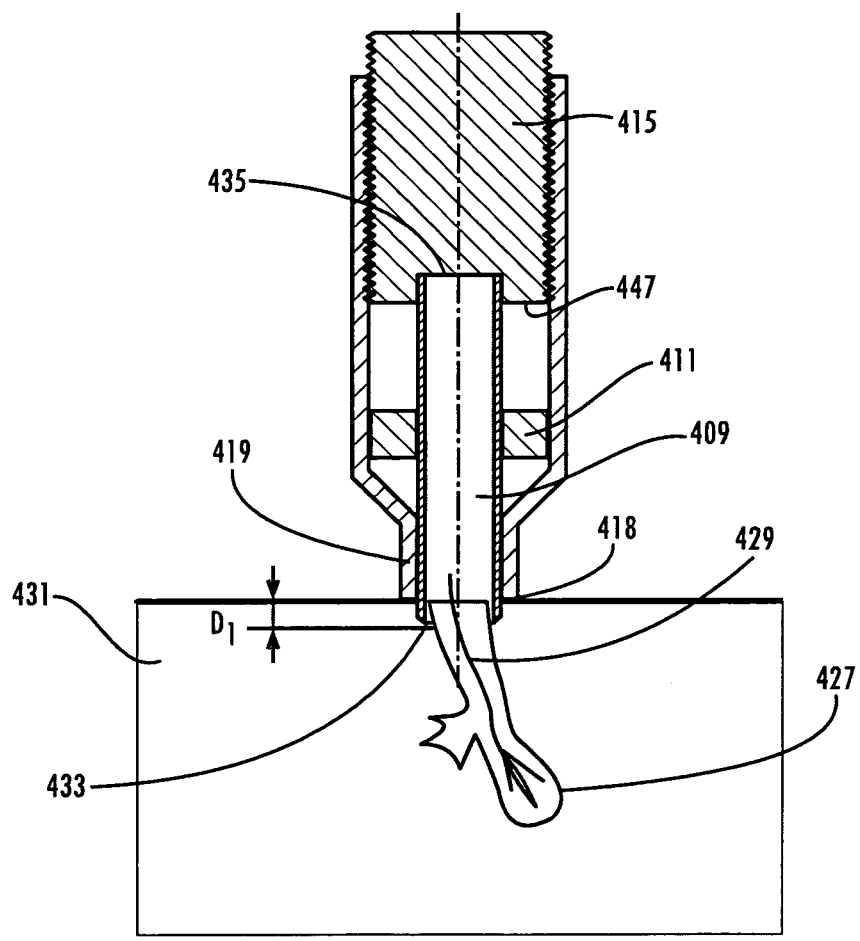
FIG. 7 is a cross-sectional view of a lower portion of an extracting instrument with a punch extending into a hair follicle according to an embodiment.

FIG. 7 illustrates a section of skin 431 containing a hair follicle sheath 427 in contact with a portion of an embodiment of an extraction instrument as described above. In this figure, an initial penetration has occurred, and a sharp or cutting end portion 433 of punch 409 has penetrated into skin 431 to a desired depth $D_1$. This figure also illustrates how nipple end 419 may act as a stop, to limit the depth of penetration by punch 409 into skin 431. Specifically, lip portion 418 may contact and/or abut the skin of a patient during the follicular extraction process and therefore aid in controlling the depth of the incision of punch 409. Here, and as illustrated above with respect to particular embodiments, such a depth of incision may be limited to the extent to which punch 409 extends beyond lip portion 418. According to a particular embodiment, lip portion 418 comprises a surface that is at a fixed distance from the sharp edge of punch 409 which abuts the skin to thereby limit the depth that punch 409 may extend beyond the surface of the skin. Adjusting the extent to which punch 409 extends beyond lip portion enables limiting the extension of punch 409 into the skin to a predetermined depth. However this is merely an example of a surface capable of limiting the extension of a punch into the skin to a predetermined depth and claimed subject matter is not so limited.

The depth of penetration is limited to the amount that punch 409 protrudes from nipple end 419, which is controllable by the surgeon by adjusting actuator 415 as illustrated herein according to particular embodiments. First end portion 435 of punch 409 is shown in assembly contact with the hole disposed at end 447 of actuator 415.

Figure 8:
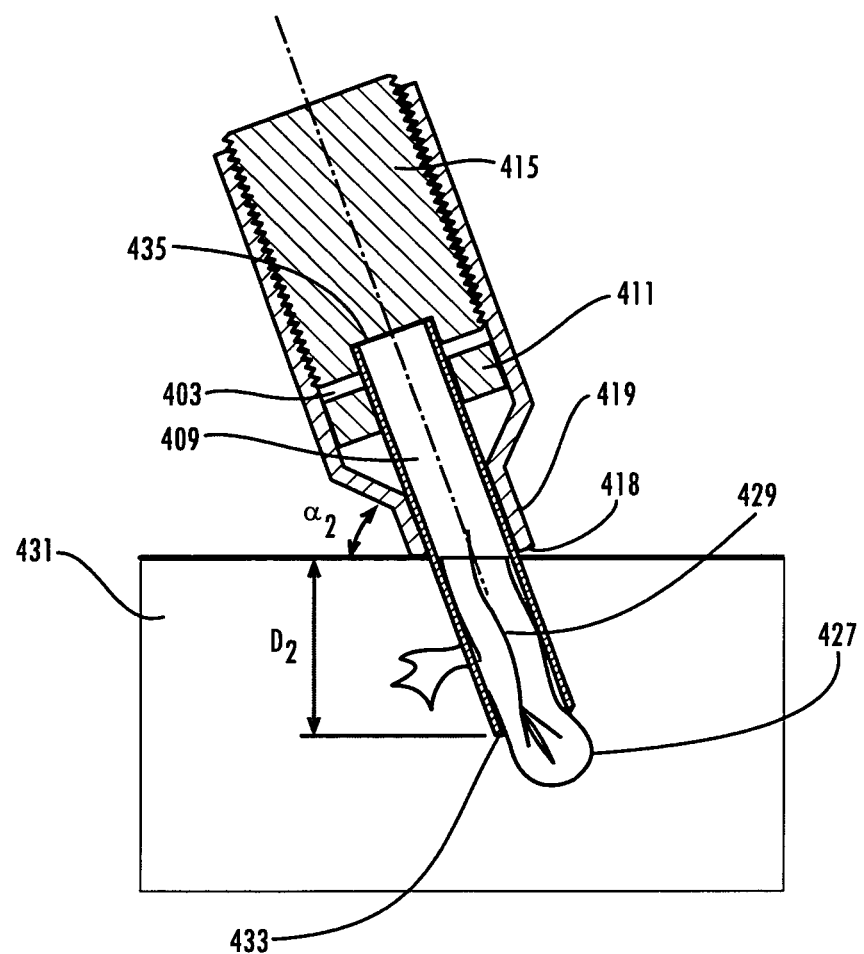
FIG. 8 is a cross-sectional view of a lower portion of an extraction instrument with a punch extending further into a hair follicle according to an embodiment.

FIG. 8 illustrates a section of skin 431 containing a hair follicle sheath 427 in contact with a portion of an embodiment of an extraction instrument as described above. As shown, sharp or cutting end portion 433 of punch 409 is at a desired depth $D_2$. This figure also illustrates how nipple end 419 acts as a stop, to limit penetration of punch 409 into skin 431. Specifically, lip portion 418 may contact and/or abut the skin of a patient during the follicular extraction process and therefore aid in controlling the depth of the incision of punch 409 by not allowing the punch to enter the skin of the patient beyond the extent to which punch 409 extends beyond lip portion 418. The depth of penetration is limited to the amount that punch 409 protrudes from nipple end 419, which is controllable by the surgeon, by adjusting actuator 415.

Referring again to FIG. 1a, in a particular embodiment, the length of punch 9 is approximately 25 millimeters, the diameter of actuator 15 is approximately 4.5 mm, the length of the actuator 15 is approximately 10 cm and diameter of the actuator head 17 is approximately 9 mm. However, in other embodiments, the actuator head 17 could be much wider and have a variety of geometrical shapes, and actuator 15 may have a variety of lengths. In one implementation, nipple end 19 is tapered, and has an outside diameter of about 4.38 mm at the top which tapers down to about 4.22 mm at the bottom, with an overall length of about 9 millimeters. In other embodiments, nipple end 19 may be of any length. In addition, main body portion 3 may be about 8 cm long and between about 6.55 and 6.67 mm in diameter. However, in yet other embodiments, main body portion 3 may be of any dimensions, wider, narrower, thinner, thicker, or shorter.

Figure 9A:
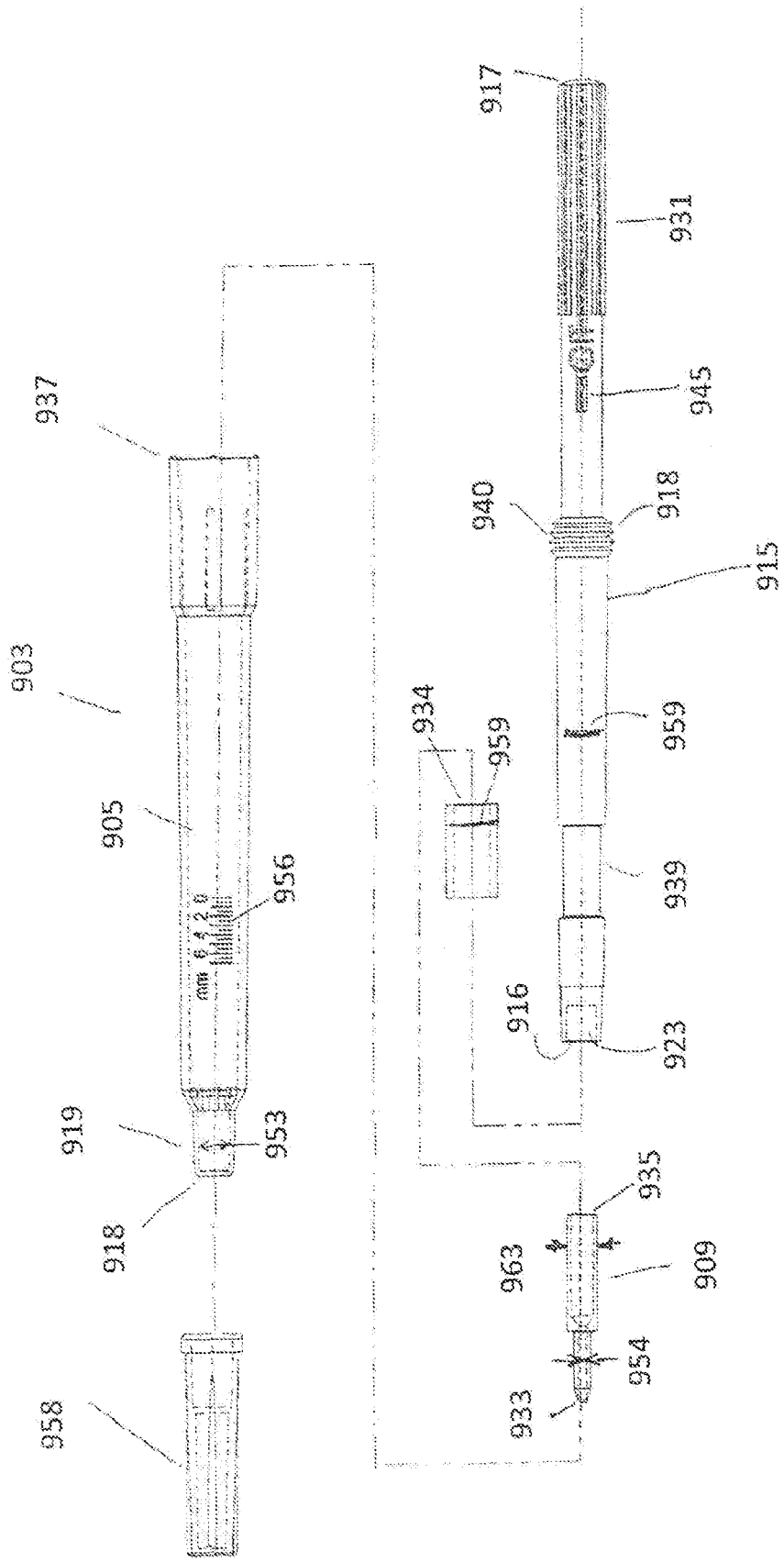
FIG. 9a is an exploded view of an extraction instrument according to an embodiment.

Referring now to FIG. 9a, in this embodiment nipple end 919 has a single diameter 953 that allows a wide variety of punch 909 diameters eliminating the need to modify the diameter of nipple 919 between each use because the diameter of end 933 of punch 909 varies according to the needs while the larger end is maintained the same as or close to the inside diameter of the nipple. The outside diameter of punch 909 may range from 0.5 mm to 7 mm. In this embodiment, a main body 903 having a substantially cylindrical shape with various diameters has a bore 905 extending longitudinally there through.

Figure 9B:
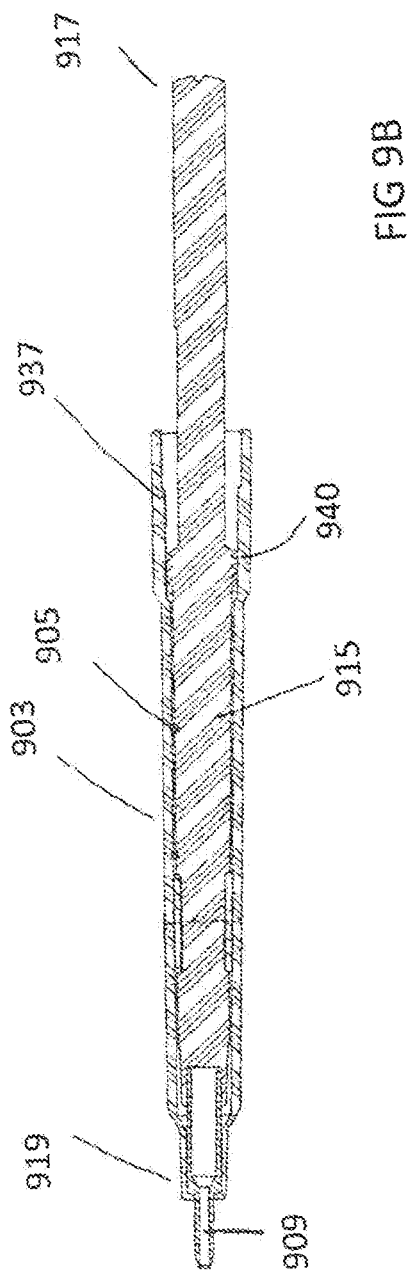
FIG. 9b is a cross-sectional view of an extraction instrument according to an embodiment.
Figure 9C:
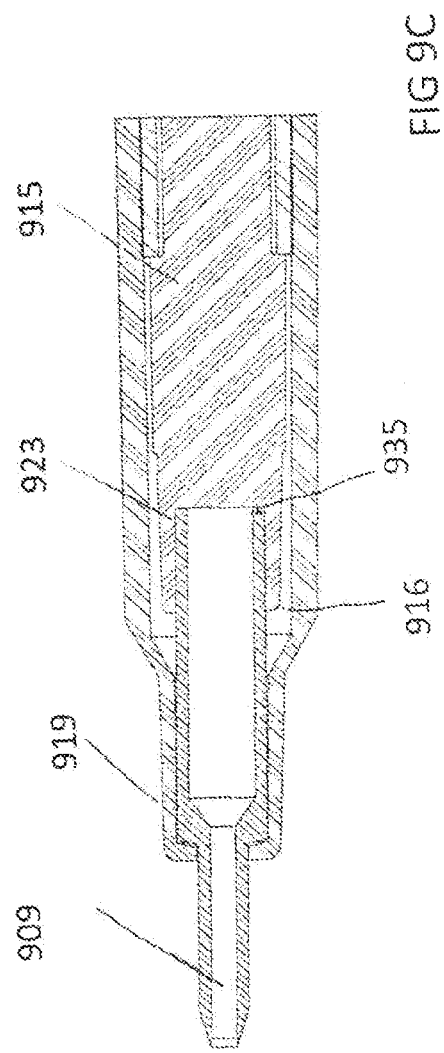
FIG. 9c is a cross-sectional view of a particular embodiment of an extraction instrument according to an embodiment in FIG. 9b.

Referring now to FIG. 9b, a nipple end 919 is disposed on one end of main body 903 and a threaded end 937 is disposed on the other end of main body 903. A portion of an actuator 915 may be disposed within bore 905. Actuator 915 having threads 940 on the outer surface for mating with threaded end 937 and actuator head 917 rotates to position actuator 915 into bore 905. As can be seen in FIG. 9c, a blind bore 923 may extend a distance longitudinally within actuator 915 but not completely through actuator 915.

Referring again to FIG. 9a, in the current embodiment, actuator 915 comprises a screw having a pitch approximately equal to 1 mm such that one full rotation results in 1 mm translation along an axis of the punch 909 and actuator 915 into bore 905. Actuator 915 may comprise one piece manufactured by, for example, injection molding or a machining process. Actuator 915 may comprise a handle 931 which may have a texture to aid the handler in gripping the device during operation. Accordingly, in this particular embodiment, displacement of actuator 915 and punch 909 along an axis of bore 905 may change substantially in proportion to rotation of actuator 915. Punch 909 may retract when actuator 915 is rotated in one direction and extend as actuator 915 is rotated in the other direction within bore 905. In another embodiment, actuator 915 may comprise any one of a variety of mechanical, hydraulic, pneumatic or electronic actuating devices, to name a few. The friction force between actuator 915 and threaded ends 937 on the inner part of main body 903 keep the actuator 915 from moving unintentionally. These are merely examples of actuating devices according to a particular embodiment and claimed subject matter is not so limited.

In a particular embodiment, actuator 915 has a first end portion 916 and second end portion 918. Referring now to FIG. 9c, first end portion 916 may comprise a blind bore 923 for assembly with the punch 909. According to a particular embodiment, first end portion 935 of punch 909 is positioned inside a blind bore 923 opening to first end portion 916 of actuator 915 and attached with a friction force or adhesive substance such as, for example, an epoxy, cyanoacrylate or silicone adhesive or by some other attachment method such as, for example, by mated threads or welding. These are merely examples of attachment methods for a punch 909 and actuator 915 and claimed subject matter is not limited in this respect.

Referring again to FIG. 9a, in the current embodiment, the first end portion 935 of punch 909 has a single diameter 963 that is larger than the sharp end portion 933. The inside diameter 954 may range from 0.7 mm to 1.45 mm, in a particular embodiment, however a range of diameters greater than and less than this range may also be used. Punch 909 may comprise any one of a variety of longitudinal lengths.

Referring again to FIG. 9a, in the current embodiment, additional stability may be provided to punch 909 due to its position relative to the inside diameter of nipple end 919 and attachment within actuator 915. Additionally, lip portion 918 may contact and/or abut the skin (not shown) of a patient during the follicular extraction process and therefore aid in controlling the depth of the incision of punch 909. In a particular embodiment, extension of actuator 915 ranges from 0 to 6 mm, however, in another embodiment actuator 915 may extend a distance greater than 6 mm. In the current embodiment, at a protrusion of distance 0 mm, the larger diameter section of punch 909 is in direct contact with the inside diameter of nipple end 919 so that at least two points of stability exist for punch 909. Protrusion of punch 909 between an extension of 0 mm and a depth of 6 mm may result in two points of contact such that punch 909 may contact nipple end 919 and actuator 915 simultaneously, in this way punch 909 remains stable throughout its range of motion. Lip portion 918 acts as a barrier preventing punch 909 from entering the skin of a patient beyond the extent to which punch 909 extends beyond lip portion 918. This aids in controlling the depth of the incision of punch 909 by preventing deeper incision of punch 909 than is intended by extension of actuator 915 to a particular extension distance. Accordingly, lip portion 918 comprises a surface that is closely (e.g. fixedly) coupled to punch 909 which abuts the skin to thereby limit the depth that punch 909 may extend beyond the surface of the skin. Adjusting the extent to which punch 909 extends beyond lip portion enables limiting the extension of punch 909 into the skin to a predetermined depth. However this is merely an example of a surface capable of limiting the extension of a punch into the skin to a predetermined depth and claimed subject matter is not so limited. Punch 909 may extend to any depth and nipple end 919 may be of any length.

In the current embodiment, punch 909 may retract or protrude 1 mm in response to one full rotation of actuator 915. Similarly, a ¼ rotation of actuator 915 causes a ¼ mm retraction or protrusion of punch 909.

Figure 9D:
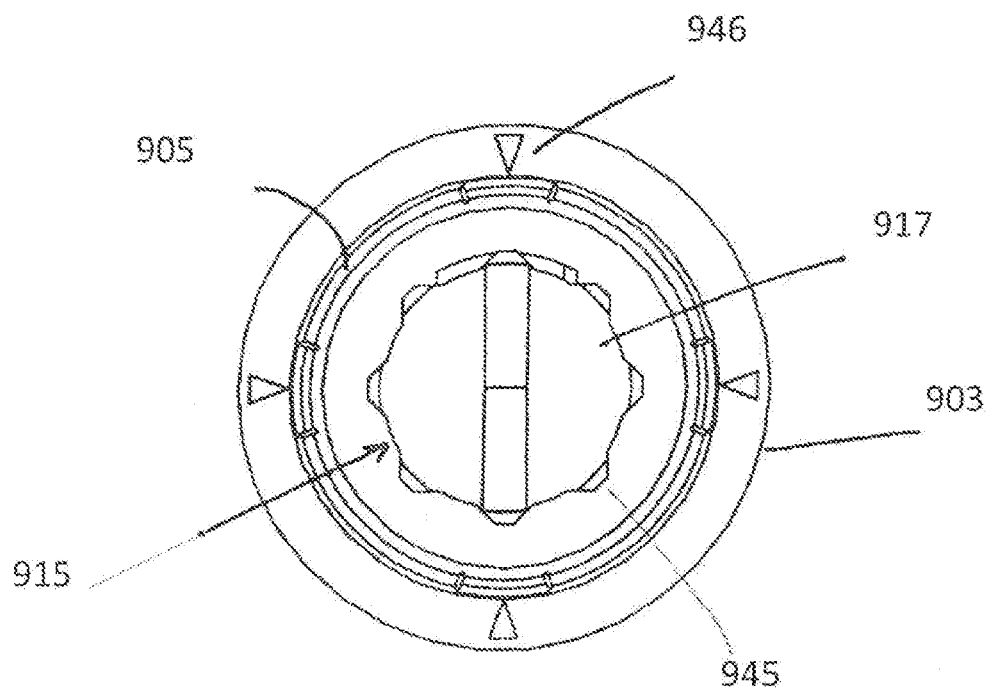
FIG. 9d is a top view of the extraction instrument as illustrated in FIG. 9a according to an embodiment.

Actuator head 917 is depicted in FIG. 9d. First depth indicator 945 is depicted on actuator 915 in FIG. 9a. FIG. 9d is an end view of a particular embodiment of actuator head 917. First depth indicators 945 shown in FIG. 9d on the head end 917 of actuator 915 such as tick marks or depressions may be aligned with second depth indicators 946 such as tick marks or depressions on the top portion of main body 903 enclosing bore 905. In the current embodiment, alignment of indicators on the head end 917 of actuator 915 with indicators on bore 905 corresponds with a particular length of retraction or protrusion of punch 909.

Referring again to FIG. 9a, a graduated scale 956 may be provided on the outside surface of main body 903. Actuator 915 may also comprise a recess 939 for placing an opaque ring 934 for contrast to the graduated scale 956. The graduated scale 956 on the main body 903 may indicate the amount of the punch 909 depth extending out of the nipple end 919. Main body 903 may comprise a substantially transparent material. In that case, the graduated scale 956 may be read against a line of demarcation 959 on actuator 915 or ring 934 so that a precise protrusion and extension depth may be noted to maintain surgical accuracy. An edge on the ring or the actuator may also be used as a line of demarcation. Ring 934 may consist of a contrasting color. When the main body 903 material is opaque, according to a particular embodiment, a narrow window (not shown) may be opened near the graduated scale 956 on the main body 903 for viewing a reference mark. In one particular embodiment graduated scale 956 may show 0.5 mm increments. Graduated scale 956 may be printed or adhesively applied to the outside of main body 903 by a variety of methods for example such as silk screening, metal etching, or by placing a removable adhesive sticker on main body 903. Further, in the current embodiment, on actuator 915 a line of demarcation 959 may be aligned with graduated scale 956 so that a precise protrusion and extension depth may be controlled and noted to maintain surgical accuracy.

Referring again to FIG. 9a, sharp or cutting end 933 of punch 909 may be covered by a protective cap 958 that fits snugly on end 916 of actuator 915. Protective cap 958 may also fit within nipple end 919 of bore 905 after actuator 915 is inserted into bore 905. In this way the sharp or cutting end 933 of punch 909 will be protected before and after it is inserted into bore 905 by the same protective cap 958.

Figure 10:
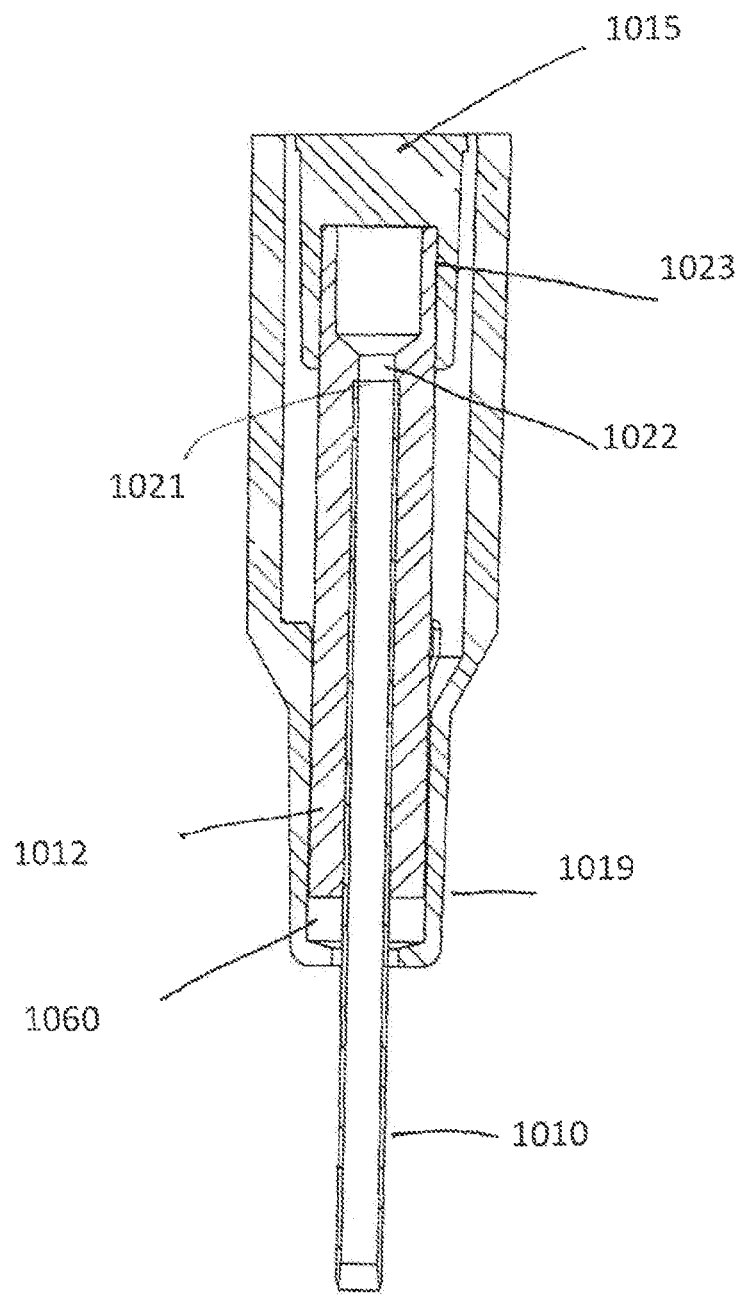
FIG. 10 is a partial section view of an extraction instrument according to an embodiment.

Referring to FIG. 10, a constant diameter cylindrical punch 1010 may be used in a particular embodiment. A hollow cylindrical adapter 1012 may enable assembly of the constant diameter cylindrical punch 1010 to actuator 1015. The constant diameter cylindrical punch 1010 may be inserted into a bore 1022 inside the adapter 1012. Bore 1022 may be adapted to position the first end 1021 of constant diameter cylindrical punch 1010 inside adapter 1012. The constant diameter cylindrical punch 1010 and adapter 1012 sub-assembly is positioned within blind bore 1023 disposed at an end of actuator 1015. Adaptor 1012 may be in contact and extend into a bore 1060 of nipple end 1019. This fit provides stabilization or limitation of lateral movements of constant diameter cylindrical punch 1010.

Figure 11:
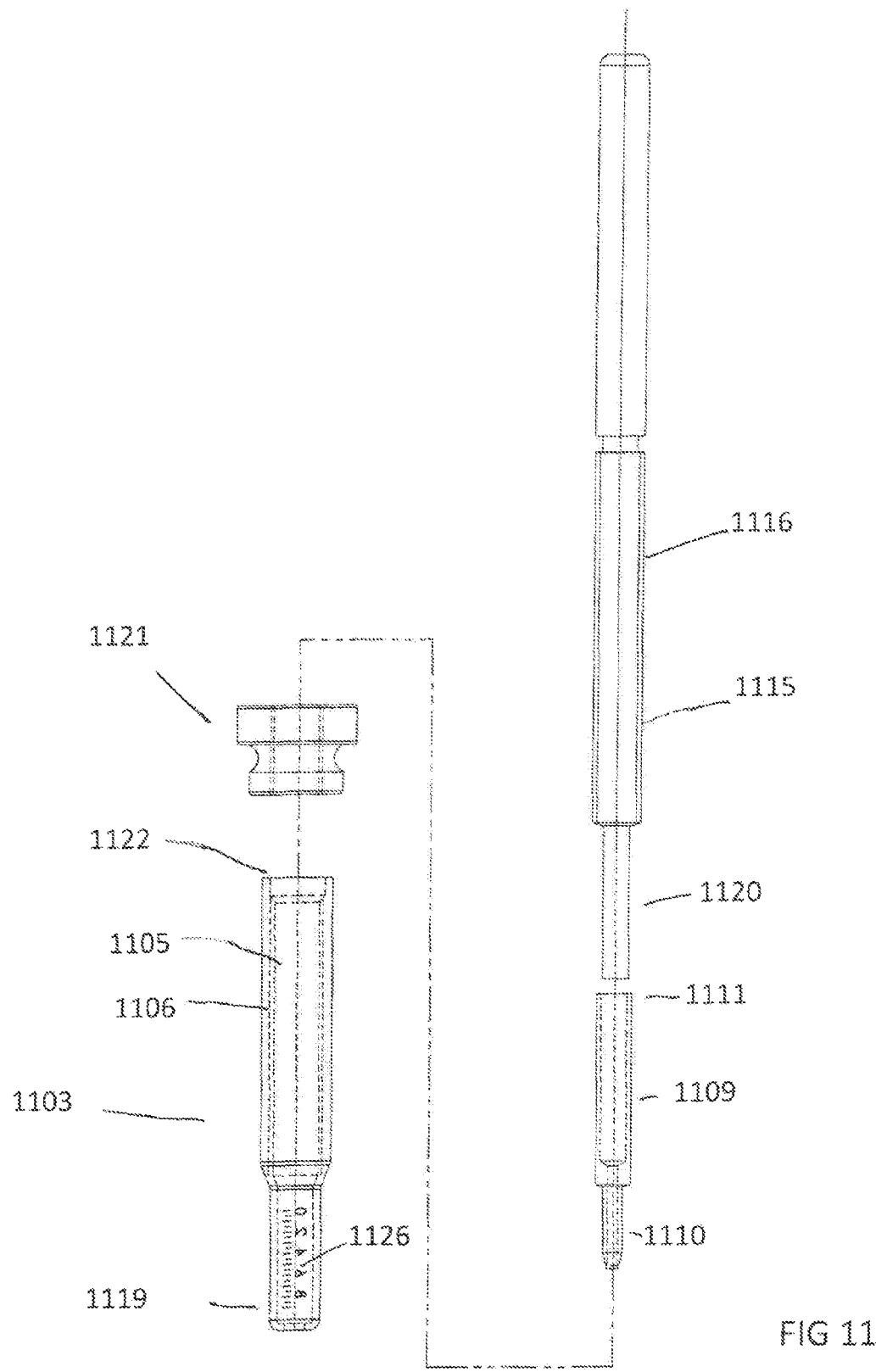
FIG. 11 is an exploded view of an extraction instrument according to an embodiment.

Referring now to FIG. 11, in a particular embodiment, a follicular extraction apparatus may have an actuator 1115 positioned within bore 1105. The bore 1105 may have threads on a portion of the inner surface 1106 of bore 1105 for mating with actuator 1115. Actuator 1115 may have threads on a portion of outer surface 1116. Actuator 1115 may have a tip portion 1120 having a diameter smaller than the diameter of outer surface 1116 for mating with a punch 1109. Punch 1109 has a first end portion 1110 and a second end portion 1111. In a particular embodiment first end portion 1110 and a second end portion 1111 may have different diameters. In a particular embodiment, the tip portion 1120 may have an outer diameter very close to the inner diameter of second end portion 1111 of punch 1109. Tip portion 1120 may be disposed within second end portion 1111 and stabilized by friction force or adhesive substance such as, for example, an epoxy, cyanoacrylate or silicone adhesive or by some other attachment method such as, for example, by mated threads, or welding. However, these are merely examples of attachment methods for a punch 1109 and actuator 1115 and claimed subject matter is not limited in this respect.

Figure 12:
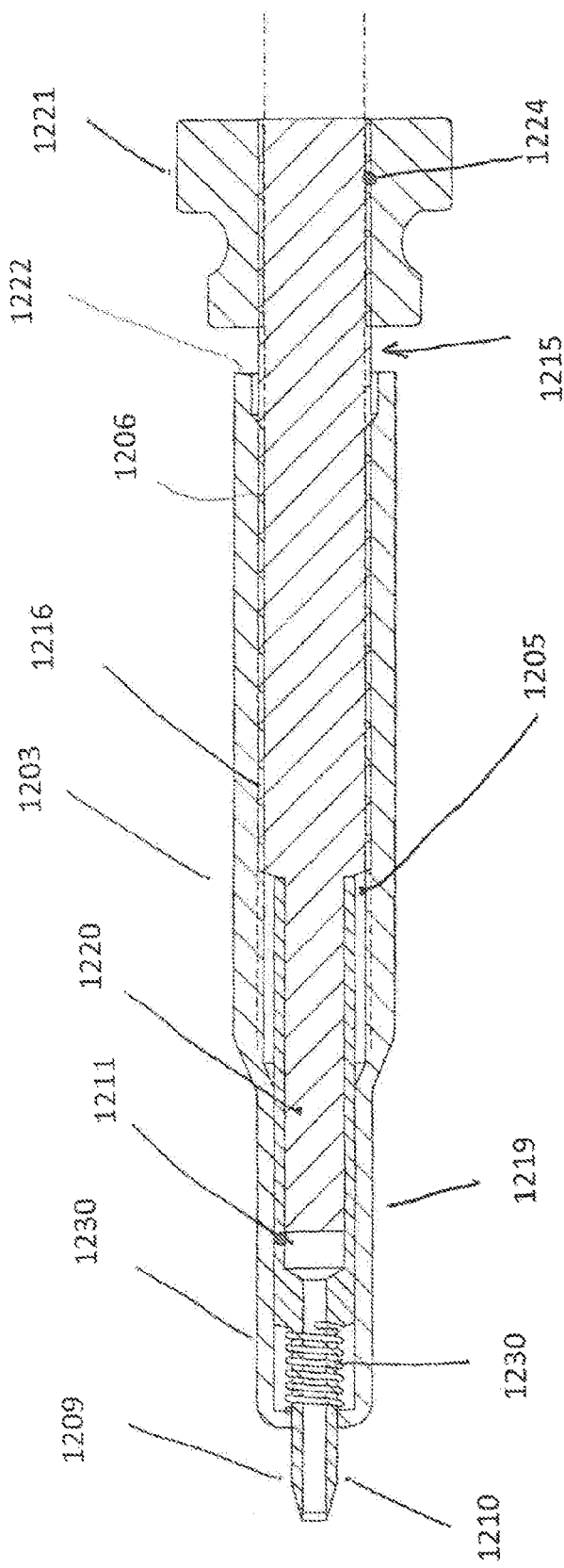
FIG. 12 is a partial cutaway view of an extraction instrument according to an embodiment.
Figure 14:
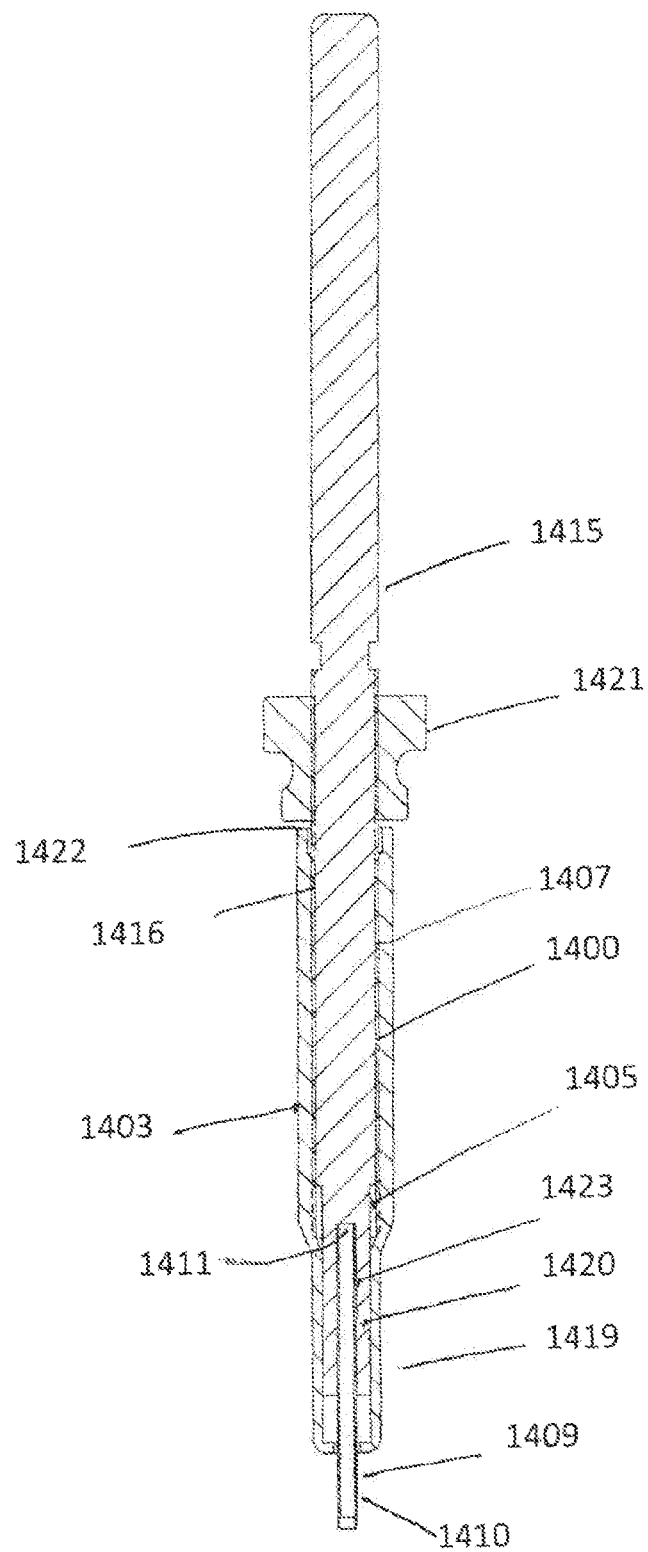
FIG. 14 is a cutaway view of an extraction instrument assembly according to an embodiment.

Punch 1109 and actuator 1115 may be positioned within a main body 1103. Main body 1103 may comprise a nipple end 1119. A locknut 1121 having threads on its inner surface may be disposed over outer surface 1116 of actuator 1115 and mated to the threads of the outer surface 1116. When a particular embodiment of the follicular extraction apparatus is assembled, locknut 1121 may be tightened by rotation until it contacts the top surface 1122 of main body 1103 as shown in FIG. 12 and FIG. 14. Locknut 1121 may stabilize main body 1103 with respect to actuator 1115. Main body 1103 may comprise a transparent material. A scale 1126 may be formed on to the side of the main body 1103 and may be used to track displacement of actuator 1115 or punch 1109. Alternatively, main body 1103 may be opaque and may have a window opening for viewing a reference edge or marking on either actuator 1115 or punch 1109 which may be used to track displacement of actuator 1115 or punch 1109.

FIGS. 11-14 show embodiments of a follicular extraction apparatus wherein a punch may be coupled to an actuator using any one of several techniques illustrated by the following examples according to particular embodiments. However, these are merely examples of how a punch may be coupled to an actuator according to particular embodiments and claimed subject matter is not so limited Referring now to FIG. 12, in a particular embodiment, a follicular extraction apparatus may have an actuator 1215 positioned within bore 1205. The bore 1205 may have threads on a portion of the inner surface 1206 of bore 1205 for mating with actuator 1215. Actuator 1215 may have threads on a portion of outer surface 1216. Actuator 1215 has a tip portion 1220 in contact with a bore (not shown) disposed in punch 1209. Punch 1209 has a first end portion 1210 and a second end portion 1211. In a particular embodiment first end portion 1210 and a second end portion 1211 may have different diameters. In a particular embodiment, the actuator tip portion 1220 may have an outer diameter smaller than the inner diameter of second end portion 1211 of punch 1209. Tip portion 1220 may be slidably disposed within second end portion 1211. In a particular embodiment, the actuator tip portion 1220 may have an outer diameter larger than the inner diameter of second end portion 1211 of punch 1209. Second end portion 1211 may be slidably disposed within tip portion 1220. Punch 1209 and actuator 1215 may be positioned within a main body 1203. Main body 1203 may comprise a nipple end 1219. A compression spring 1230 may be disposed longitudinally within the nipple end 1219 providing a stabilizing force on punch 1209. A locknut 1221 having threads 1224 on its inner surface may be disposed over outer surface 1216 of actuator 1215 and mated to the threads of outer surface 1216. When a particular embodiment of the follicular extraction apparatus is assembled, locknut 1221 may be tightened by rotation until it contacts the top surface 1222 of main body 1203. Locknut 1221 may stabilize actuator 1215 with respect to main body 1203. Main body 1203 may comprise a substantially transparent material. The above description merely provides examples of assembly and attachment methods for a follicular extraction apparatus according to particular embodiments, and claimed subject matter is not limited in this respect.

Figure 13:
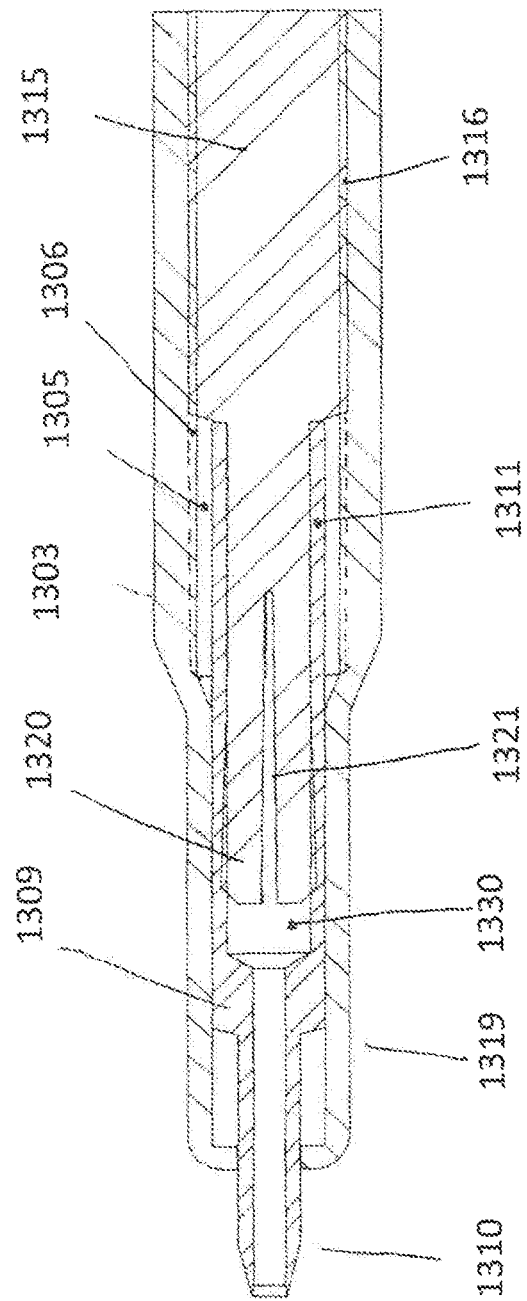
FIG. 13 is a partial cutaway view of an extraction instrument according to an embodiment.

Referring now to FIG. 13, in a particular embodiment, a follicular extraction apparatus may have an actuator 1315 positioned within bore 1305. The bore 1305 may have threads on a portion of the inner surface 1306 of bore 1305 for mating with actuator 1315. Actuator 1315 may have threads on a portion of outer surface 1316. Punch 1309 has a first end portion 1310 and a second end portion 1311. Actuator 1315 may have a tip portion 1320 with a bifurcation 1321. Bifurcation 1321 permits deformation of tip portion 1320 such that tip portion 1320 may be positioned within bore 1330 of punch 1309. Bifurcation 1321 may also permit a compression fit between bore 1330 and tip portion 1320. In a particular embodiment, first end portion 1310 and a second end portion 1311 may have different diameters. Tip portion 1320 may be disposed within second end portion 1311. Punch 1309 and actuator 1315 may be positioned within a main body 1303. Main body 1303 may comprise a nipple end 1319. Similarly to FIG. 11, the assembly of the current embodiment includes a locknut 1121 having threads on its inner surface may be disposed over outer surface 1116 of actuator 1115 and mated to the threads of outer surface 1116. When a particular embodiment of the follicular extraction apparatus is assembled, locknut 1121 may be tightened by rotation until it contacts the top surface 1122 of main body 1103. Locknut 1121 may stabilize actuator 1115 with respect to main body 1103. Main body 1103 may comprise a substantially transparent material. A scale 1126 may be formed to the side of the main body 1103 and may be read against a reference edge or marking on either actuator 1115 or punch 1109. Alternatively, main body 1103 may be opaque and may have a window opening for viewing a reference edge or marking on either actuator 1115 or punch 1109. The above description provides examples of assembly and attachment methods for a follicular extraction apparatus and claimed subject matter is not limited in this respect.

Referring now to FIG. 14, in a particular embodiment, a follicular extraction apparatus may have an actuator 1415 positioned within bore 1405. The bore 1405 may have threads 1407 on a portion of the inner surface 1406 of bore 1405 for mating with actuator 1415. Actuator 1415 may have threads on a portion of outer surface 1416. Punch 1409 has a first end portion 1410 and a second end portion 1411. Actuator 1415 may have a tip portion 1420 having a blind bore 1423 for mating with a punch 1409. Blind bore 1423 may have an inner diameter very close to the outer diameter of second end portion 1411 of punch 1409. Second end portion 1411 may be positioned within blind bore 1423. Assembly of punch 1409 to actuator 1415 may be done using adhesives like epoxy or mechanical attachments like threading or welding. In a particular embodiment, first end portion 1410 and a second end portion 1411 may have substantially equivalent diameters. Punch 1409 and actuator 1415 may be positioned within a main body 1403. Main body 1403 may comprise a nipple end 1419 having a diameter smaller than the diameter of main body 1403. Locknut 1421 having threads (not shown) on its inner surface may be disposed over outer surface 1416 of actuator 1415 and mated to threads of the outer surface 1416. When a particular embodiment of the follicular extraction apparatus is assembled, locknut 1421 may be tightened by rotation until it contacts the top surface 1422 of main body 1403. Locknut 1421 may stabilize actuator 1415 with respect to main body 1403. Main body 1403 may comprise a substantially transparent material. The above description provides examples of assembly and attachment methods for a follicular extraction apparatus and claimed subject matter is not limited in this respect.

While certain features of claimed subject matter have been illustrated as described herein, many modifications, substitutions, changes and equivalents will now occur to those skilled in the art. It is, therefore, to be understood that the appended claims are intended to cover all such embodiments and changes as fall within the true spirit of claimed subject matter.

What is claimed is:

1. An apparatus comprising:
   a main body comprising a first bore disposed between first and second ends of said main body;
   a nipple portion comprising a first end portion coupled to said first end of said main body and a tip portion, the nipple portion comprising a second bore disposed within said tip portion;
   a punch, having an interior surface, for extracting one or more hair follicles along said interior surface of said punch, said punch comprising a first punch end and a second punch end and having a substantially cylindrical shape slidably disposed within said second bore, and wherein said punch comprises a substantially uniform cylindrical cutting edge positioned substantially perpendicular to an axis extending between said first and second ends of said punch;
   an actuator in direct communication with said first end of said punch to displace said punch along an axis of said second bore, in response to adjustment of said actuator, to fix a distance by which said second punch end portion extends beyond said tip portion of said nipple portion; and
   a stabilizer disposed within said main body between said nipple portion and said actuator, wherein said punch extends through a bore of said stabilizer, said stabilizer having an outer surface, a substantially full length of said outer surface being in direct communication with an interior surface of said main body.

2. The apparatus of claim 1, wherein displacement of said actuator along said axis is controlled by rotation of said actuator about said axis.

3. The apparatus of claim 2, wherein said displacement of said actuator along said axis is capable of changing substantially proportionally with respect to said rotation.

4. The apparatus of claim 1, wherein said second end of said punch comprises a flat end or an angled end.

5. The apparatus of claim 1, wherein said punch is translatable along said axis in response to rotation of said actuator.

6. The apparatus of claim 1, wherein said nipple portion further comprises an inner surface and wherein said second end of said punch is in communication with at least a portion of said inner surface of said nipple portion.

7. The apparatus of claim 2, wherein displacement of said punch along said axis is adjustable in a range between 0 and 8 mm in response to rotation of said actuator.

8. The apparatus of claim 1, wherein said actuator further comprises a head portion having at least one first depth indicator.

9. The apparatus of claim 8, wherein said first end of said main body further comprises at least one second depth indicator capable of alignment with said first depth indicator.

10. The apparatus of claim 1, wherein a first diameter of said first end of said punch is greater than a second diameter said second end of said punch.

11. The apparatus of claim 1, wherein said main body further comprises a visible graduated scale.

12. The apparatus of claim 10, wherein said actuator further comprises an indicator capable of aligning with a graduated scale.

13. The apparatus of claim 1, wherein said tip portion further comprises a lip portion capable of contacting skin of a patient.

14. The apparatus of claim 13, wherein said lip portion limits the depth of penetration of said punch into the skin of a patient.

15. The apparatus of claim 13, wherein the second end of the punch extends beyond the lip portion a predetermined length.

16. The apparatus of claim 1, wherein displacement of said actuator along said axis is controllable in response to a mechanical force acting on said actuator.

17. The apparatus of claim 1, wherein displacement of said actuator along said axis is controllable in response to a hydraulic force acting on said actuator.

18. The apparatus of claim 1, wherein displacement of said actuator along said axis is controllable in response to a pneumatic force acting on said actuator.

19. The apparatus of claim 1, wherein displacement of said actuator along said axis is controllable in response to an electromagnetic force acting on said actuator.

20. The apparatus of claim 1, further comprising a ring disposed over said actuator.

* * * * *